United States Patent
Clay et al.

(10) Patent No.: US 10,450,317 B2
(45) Date of Patent: Oct. 22, 2019

(54) NOTCH PATHWAY SIGNALING INHIBITOR COMPOUNDS

(71) Applicants: Eli Lilly and Company, Indianapolis, IN (US); Audion Therapeutics, Amsterdam (NL)

(72) Inventors: Julia Marie Clay, Indianapolis, IN (US); Albert Edge, Brookline, MA (US); Philip Arthur Hipskind, New Palestine, IN (US); John C. Gill, Boston, MA (US); Bharvin Kumar Patel, Carmel, IN (US); Helmuth Hendrikus Gerardus Van Es, Virac (FR); Aaron D. Wrobleski, Indianapolis, IN (US); Gaiying Zhao, Carmel, IN (US)

(73) Assignees: Eli Lilly and Company, Indianapolis, IN (US); Audion Therapeutics, Amsterdam (NL)

( * ) Notice: Subject to any disclaimer, the term of this patent is extended or adjusted under 35 U.S.C. 154(b) by 0 days.

(21) Appl. No.: 15/736,345

(22) PCT Filed: Jul. 1, 2016

(86) PCT No.: PCT/US2016/040612
§ 371 (c)(1),
(2) Date: Dec. 14, 2017

(87) PCT Pub. No.: WO2017/007702
PCT Pub. Date: Jan. 12, 2017

(65) Prior Publication Data
US 2018/0148456 A1 May 31, 2018

Related U.S. Application Data

(60) Provisional application No. 62/189,393, filed on Jul. 7, 2015.

(51) Int. Cl.
| | | |
|---|---|---|
| C07D 487/04 | (2006.01) | |
| C07D 487/14 | (2006.01) | |
| C07D 471/14 | (2006.01) | |
| A61P 35/02 | (2006.01) | |
| A61P 27/16 | (2006.01) | |
| A61P 35/00 | (2006.01) | |

(52) U.S. Cl.
CPC ............ *C07D 487/04* (2013.01); *A61P 27/16* (2018.01); *A61P 35/00* (2018.01); *A61P 35/02* (2018.01); *C07D 471/14* (2013.01); *C07D 487/14* (2013.01); *C07B 2200/07* (2013.01)

(58) Field of Classification Search
CPC ......... C07D 487/04; A61P 35/00; A61P 27/16
See application file for complete search history.

(56) References Cited

U.S. PATENT DOCUMENTS

| | | |
|---|---|---|
| 8,188,131 B2 | 5/2012 | Edge et al. |
| 8,569,286 B2 | 10/2013 | Hipskind et al. |
| 8,716,229 B2 | 5/2014 | Stankovic et al. |
| 8,859,597 B2 | 10/2014 | Edge et al. |
| 2009/0124568 A1 | 5/2009 | Heller et al. |
| 2009/0297533 A1 | 12/2009 | Lichter et al. |
| 2013/0029972 A1 | 1/2013 | Hipskind et al. |
| 2013/0236477 A1 | 9/2013 | Edge |

FOREIGN PATENT DOCUMENTS

| | | |
|---|---|---|
| WO | 2007/110335 A1 | 10/2007 |
| WO | 2010/060088 A2 | 5/2010 |
| WO | 2014/039781 A1 | 3/2014 |
| WO | 2014/071275 A1 | 5/2014 |
| WO | 2017/007702 A1 | 1/2017 |
| WO | WO-2018111926 A2 * | 6/2018 ............. A61K 45/06 |

OTHER PUBLICATIONS

American Cancer Society. "Breast Cancer." (2014), Accessed Nov. 9, 2018. Available from: < https://www.cancer.org/cancer/breast-cancer/risk-and-prevention.html >. (Year: 2014).*
NavigatingCancer.com. "List of Cancer Chemotherapy Drugs." (2013). Accessed Nov. 9, 2018. Available from: < https://www.navigatingcare.com/library/all/chennotherapy_drugs >. (Year: 2013).*
Mayo Clinic. "Pancreatic Cancer." (Apr. 10, 2012). Accessed Nov. 9, 2018. Available from: < https://www.mayoclinic.org/diseases-conditions/pancreatic-cancer/symptoms-causes/syc-20355421?p=1 >. (Year: 2012).*
UCSF Medical Center. "Liver Cancer." (Mar. 8, 2005), Accessed Nov. 9, 2018. Available from: < https://www.ucsfhealth.org/conditions/liver_cancer/ >. (Year: 2005).*

(Continued)

*Primary Examiner* — Andrew D Kosar
*Assistant Examiner* — John S Kenyon
(74) *Attorney, Agent, or Firm* — Grant E Reed

(57) ABSTRACT

The present invention provides the following compounds, or pharmaceutically acceptable salts thereof, and pharmaceutical compositions containing said compounds useful as a Notch pathway signaling inhibitor for the treatment of named cancers, sensorineural hearing loss caused by auditory hair cell loss, and inducing auditory hair cell generation.

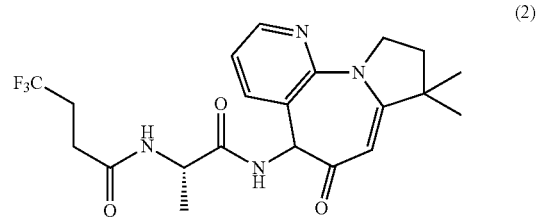

(2)

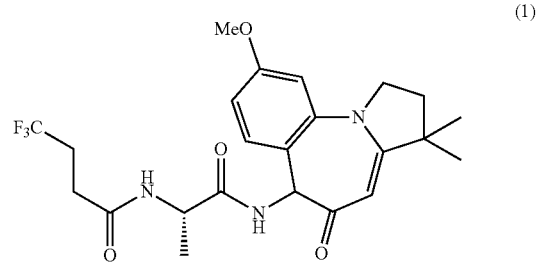

(1)

12 Claims, No Drawings
Specification includes a Sequence Listing.

(56) References Cited

OTHER PUBLICATIONS

Guo, H., et al. "Targeting the Notch signaling pathway in cancer therapeutics." Thoracic Cancer. (2014), vol. 5, pp. 473-486. (Year: 2014).*
Murata, J., et al. "Notch Signaling and the Developing Inner Ear." Notch Signaling in Embryology and Cancer. (2011). (Year: 2011).*
Fattorusso, Caterina, et al., "Specific Targeting Highly Conserved Residues in the HIV-1 Reverse Transcriptase Primer Grip Region. Design, Synthesis, and Biological Evaluation of Novel, Potent, and Broad Spectrum NNRTIs with Antiviral Activity," *J. Med. Chem.* 48: 7153-7165 (2005).
Salt, Alec N., "Principles of Local Drug Delivery to the Inner Ear", Audiology & Neurotology, vol. 14, (2009).
Kelley, Matthew W., "Regulation of cell fate in the sensory epithelia of the inner ear" Nature Reviews, Neuroscience, vol. 7 (2006).
Parker, Mark A.., "The Potential Use of Stem Cells for Cochlear Repair", Audiology & Neuro-Otology, vol. 9 (2004).
Torchinsky, C., "Regulation of p27Kip1 during gentamicin mediated hair cell death", Journal of Neurocytology, vol. 28 (1999).
Lowenheim, Hubert, et al., "Gene disruption of $p27^{Kip1}$ allows cell proliferation in the postnatal and adult organ of Corti", Proceedings of the National Academy of Sciences, USA, vol. 96 (1999).
Minoda, Ryosei, et al., "Manipulating cell cycle regulation in the mature cochlea", Hearing Research, vol. 232 (2007).
Lumpkin, Ellen A., "Math1-driven GFP expression in the developing nervous system of transgenic mice" Gene Expression Patterns, vol. 3 (2003).
Mizutari, Kunio, et al., "Notch Inhibition Induces Cochlear Hair Cell Regeneration and Recovery of Hearing after Acoustic Trauma", Neuron, vol. 77 (2013).
Oshima, Kazuo, et al., "Isolation of Sphere-Forming Stem Cells from the Mouse Inner Ear", Methods and Protocols, vol. 493 (2009).
Kazanjian, Avedis, et al., "Atonal Homolog 1 is Required for Growth and Differentiation Effects of Notch/γ-Secretase Inhibitors on Normal and Cancerous Intestinal Epithelial Cells" Gastroenterology, vol. 139, (2010).
Korrapati, Soumya, et al., "Notch Signaling Limits Supporting Cell Plasticity in the Hair Cell-Damaged Early Postnatal Murine Cochlea", Plos One, vol. 8, (Aug. 2013).
Parker, Mark, et al., "Primary Culture and Plasmid Electroporation of the Murine Organ of Corti." Journal of Visualized Experiments, vol. 36 (2010).
Quadir, Anisul, "Characterization of Newly Developed Micronized Poloxamers for Poorly Soluble Drugs", BASF The Chemical Company, Pharma Solutions (2005).
Macdonald, Glen H., et al., "Three-dimensional imaging of the intact mouse cochlea by fluorescent laser scanning confocal microscopy", Hearing Research, vol. 243 (2008).
Lin, Vincent, et al., "Inhibition of Notch Activity Promotes Nonmitotic Regeneration of Hair Cells in the Adult Mouse Utricles", The Journal of Neuroscience, vol. 31 (2011).
Haynes, David. S., "Intratympanic Dexamethasone for Sudden Sensorineural Hearing Loss After Failure of Systemic Therapy", The Laryngoscope, vol. 117 (2007).
Kara, Emrah, et al., "Modified intratympanic treatment for idiopathic sudden sensorineural hearing loss", European Archives of Otorhinolaryngol, vol. 267 (2010).
Labatut, Tomas, et al., "Intratympanic steroids as primary initial treatment of idiopathic sudden sensorineural hearing loss", European Archives of Otorhinolaryngol, vol. 270 (2013).
Kelley, MW, et al., "The developing organ of Corti contains retinoic acid and forms supernumerary hair cells in response to exogenous retinoic acid in culture", Development, vol. 119, (1993).
Kwan, Tao, et al., "Development and Regeneration of the Inner Ear Cell Cycle Control and Differentiation of Sensory Progenitors", International Symposium on Olfaction and Taste, vol. 1170 (2009).
Parker, Mark, A., "Biotechnology in the Treatment of Sensorineural Hearing Loss: Foundations and Future of Hair Cell Regeneration", Journal of Speech Language and Hearing Research, vol. 54 (2011).
Peters, Jens-Uwe, et al., "Novel orally active, dibenzazepinone-based γ-secretase inhibitors", Bioorganic & Medicinal Chemistry Letters, vol. 17 (2007).
Tona, Yosuke, et al., "Therapeutic potential of a gamma-secretase inhibitor for hearing restoration in a guinea pig model with noise-induced hearing loss", BMC Neuroscience, vol. 15 (2014).
Wang, Guo-Peng, et al., "Notch signaling and Atoh1 expression during hair cell regeneration in the mouse utricle", Hearing Research, vol. 267 (2010).
Izumikawa, Masahiko, et al., "Auditory hair cell replacement and hearing improvement by Atoh1 gene therapy in deaf mammals", Nature Medicine vol. 11, (2005).
Grabher, Clemens, et al., "Notch 1 activation in the molecular pathogenesis of T-cell acute lymphoblastic leukaemia" Nature Reviews Cancer, vol. 6 (2006).
Weng, Andrew P., et al., "Activating Mutations of NOTCH1 in Human T Cell Acute Lymphoblastic leukemia", Science, vol. 306 (2004).
Rosati, Emanuela, et al., "Constitutively activated Notch signaling is involved in survival and apoptosis resistance of B-CLL cells", Blood, vol. 113, (2009).
Sliwa, Thamer, et al., "Hyperexpression of NOTCH-1 is found in immature acute myeloid leukemia" International Journal of Clinical & Experimental Pathology, vol. 7 (2014).
Nakahara, Fumio, et al, "Hes1 immortalizes committed progenitors and plays a role in blast crisis transition in chronic myelogenous leukemia", Blood, vol. 115, (2010).
Robert-Moreno, A, et al., "The notch pathway positiviely regulates programmed cell death during erythroid differentiation", Leukemia, vol. 21 (2007).
Stoeck, Alexander, et al., "Discovery of Biomarkers Predictive of GSI Response in Triple-Negative Breast Cancer and Adenoid Cystic Carcinoma", Cancer Discovery, vol. 4, (2014).
Park, Joon, T., et al., "Notch3 Gene Amplification in Ovarian Cancer", Cancer Research, vol. 66, (2006).
Gast, Andreas, et al., "Somatic Alterations in the Melanoma Genome: A High-Resolution Array-Based Comparative Genomic Hybridization Study", Genes, Chromosones & Cancer, vol. 49, (2010).
Westhoff, Britta, et al., "Alterations of the Notch pathway in lung cancer", PNAS, vol. 106 (2009).
Rangathan, Prathibha, et al., "Notch signaling in solid tumours: a little bit of everything but not all the time", Nature Review Cancer, vol. 11, (2011).
Rangathan, Prathibha, et al., Supplemental Table S1 (2011).
Belyea, Brian C., et al., "Inhibition of the Notch-Hey1 Axis Blocks Embryonal Rhabdomyosarcoma Tumorigenesis", Clinical Cancer Research, vol. 17 (2011).
Roma, Josep, et al., "Notch Pathway Inhibition Significantly Reduces Rhabdomyosarcoma Invasiveness and Mobility In Vitro", Clinical Cancer Research, vol. 17, (2010).
Wang, Chang Ye Yale, et al., "Hedgehog and Notch Signaling Regulate Self-Renewal of Undifferentiated Pleomorphic Sarcomas", Cancer Research, vol. 72, (2012).
Villanueva, Augusto, et al., "Notch Signaling is Activated in Human Hepatocellular Carcinoma and Induces Tumor Formation in Mice", Gastroenterology, vol. 143 (2012).
Yoon, Hyun Ah, et al., "Clinicopathological significance of altered Notch signaling in extrahepatic cholangiocarcinoma and gallbladder carcinoma" World Journal of Gastroenterology, vol. 17 (2011).
Bell, Diana, et al., "Expression and significance of notch signaling pathway in salivary adenoid cystic carcinoma" Annals of Diagnostic Pathology, vol. 18 (2014).
Shih, le-Ming, et al., "Notch Signaling, γ-Secretase Inhibitors, and Cancer Therapy" Cancer Research, vol. 67 (2007).
Helms, Amy W., et al., "Autoregulation and multiple enhancers control Math1 expression in the developing nervous system", Development, vol. 127, (2000).
Kawamoto, Kohei, et al., "Math1 Gene Transfer Generates New Cochlear Hair Cells in Mature Guinea Pigs In Vivo", The Journal of Neuroscience, vol. 23 (2003).
Ravi, V., et al., "Identification of therapeutic targets in angiosarcoma", Journal of Clinical Oncology, vol. 25, (2007).

(56) References Cited

OTHER PUBLICATIONS

Sekiya, Sayaka, et al., "Intrahepatic cholangiocarcinoma can arise from Notch-mediated conversion of hepatocytes", Journal of Clinical Investigation, vol. 122 (2012).
Meng, R.D., et al., "Association of Notch signaling pathway expression in liposarcomas with outcome, and targeting with gamma-secretase inhibitors" Journal of Clinical Onoclogy, vol. 27, 15S Suppl. (2009).
Zheng, Lisa J., et al., "Overexpression of Math1 induces robust production of extra hair cells in postnatal rat inner ears", Nature, vol. 3, (2000).
Wu, Wen-Rui, et al., "Clinicopathological significance of aberrant Notch receptors in intrahepatic cholangiocarcinoma", International Journal of Clinica & Experimental Pathology, vol. 7, (2014).

* cited by examiner

NOTCH PATHWAY SIGNALING INHIBITOR COMPOUNDS

Loss of the sensory hair cells in the inner ear through aging, exposure to noise, exposure to chemical agents, medications, disease, and genetic disorders cause hearing disorders in many people each year. Regardless of the etiology, the death or dysfunction of mechanosensory hair cells located within the organ of Corti of the cochlea is the primary cause of sensorineural hearing loss (SNHL). Prophylactic measures to inhibit hearing loss are primarily limited to peripheral protection, such as ear plugs or noise reduction or cancelling headphones. Current treatments for SNHL are primarily based on electronic technologies such as amplification of sound using hearing aids or bypassing the hair cells through electrical stimulation of the surviving spiral ganglion neurons using cochlear implants. Steroid administration, to afford systemic therapy or intratympanic therapy have also been suggested for sudden sensorineural hearing loss.

The cochlear sensory epithelium contains hair cells adapted for the detection of sound vibration, which is transduced by stereocilia at the hair cell's apical surfaces into electrical impulses and transmitted to the brain through the VIIIth cranial nerve. Auditory hair cells produced during development are post-mitotic and are not replaced after loss or as part of normal cell turnover in mammals. As a result, SNHL due to auditory hair cell loss is irreversible. Auditory hair cell development during the embryonic period includes a differentiation, in which prosensory epithelial cells acquire different fates, either hair cell or supporting cell, through a process of lateral inhibition which is mediated by Notch signaling. Prosensory epithelial cells are prevented from differentiating into hair cells by active Notch signaling stimulated by ligands on adjacent hair cells. These cells become supporting cells.

Notch signaling is an evolutionary conserved pathway that plays an integral role in development and tissue homeostasis in mammals. The Notch receptors and ligands contain single-pass transmembrane domains, are expressed on the cell surface and, for that reason, Notch signaling is particularly important in mediating communication between adjacent cells expressing the receptors and ligands. There are four known Notch receptors found in rodents and humans, termed. Notch 1 to Notch 4. The Notch receptors are heterodimeric proteins composed of extracellular and intracellular domains that are initially synthesized as a single polypeptide. Receptor-ligand interaction triggers a series of proteolytic cleavages of the Notch receptor polypeptide in which γ-secretase activity is involved. γ-Secretase activity cleaves Notch intracellular domain from the internal side of the plasma membrane which translocates to the nucleus to form a transcription factor complex. Notch intracellular domain (NICD) is the active form of the protein. Various Notch signaling functions include proliferation, differentiation, apoptosis, angiogenesis, migration and self-renewal. These diverse roles of Notch signaling during the development and maintenance of normal tissues can be aberrantly activated in different forms of cancer. The oncogenic functions of Notch signaling include the inhibition of apoptosis and the promotion of cell proliferation.

γ-Secretase plays a pivotal role in the Notch activation cascade. As a result, inhibitors of γ-secretase have been actively investigated for their potential to block Notch receptor activation for the treatment of cancer. No commercial Notch inhibitor chemotherapeutic drugs have emerged although clinical trials are continuing.

γ-Secretase, through the Notch signaling pathway, also plays a pivotal role in prosensory cell differentiation. As a result, inhibitors of γ-secretase have been actively investigated for their potential to block Notch receptor activation for the treatment of SNHL. Rather than administering a Notch inhibiting agent by various methodologies for entry into systemic circulation to induce atonal homolog 1 (Atoh1 or Math1) expression at abnormally elevated levels and for extended periods of time, it would be useful and desirable to induce Atoh1 expression, in the cochlear environment, at a more targeted expression level and period of time. The inability to modulate Atoh1 remains an obstacle to research in auditory hair cells and the development of therapeutics for auditory hair cell regeneration. Although research continues, such as WO 2014/039781, no commercial Notch inhibitor for treating sensorineural hearing loss caused by auditory hair cell loss has emerged.

There is a need to find compounds having Notch pathway signaling inhibitory activity. There is a further need to find compounds which inhibit Notch pathway signaling by γ-secretase inhibitory activity. There is also a need to find compounds possessing distinct structural features that may contribute to Notch pathway signaling and γ-secretase inhibitory activity. A further need is to find compounds that induce Atoh1 expression by inhibiting Notch pathway signaling. There is a further need to find compounds demonstrating desirable absorption, distribution, metabolism and excretion properties.

One aspect of the invention is to provide a compound of the structure:

Compound 1

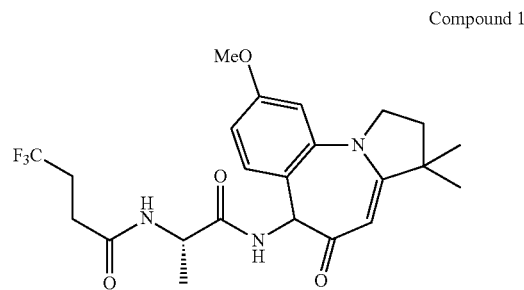 [SMILES: COc1ccc2c(c1)N1CCC(C)(C)C1=CC(=O)C2NC(=O)[C@H](C)NC(=O)CCC(F)(F)F]

4,4,4-trifluoro-N-((2S)-1-((9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide, or a substantially diastereomerically pure isomer thereof, or a pharmaceutically acceptable salt of any of the above.

A further aspect of the invention is a compound of the structure:

Compound 2

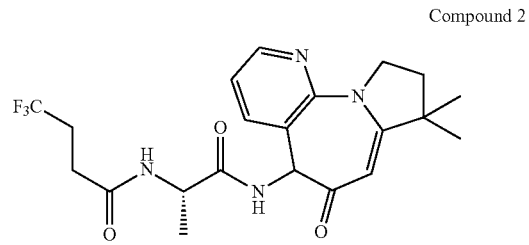 [SMILES: C[C@H](NC(=O)CCC(F)(F)F)C(=O)NC1C(=O)C=C2N(CCC2(C)C)c2ncccc21]

N-((2S)-1-((8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide, or a substantially diastereomerically pure isomer thereof, or a pharmaceutically acceptable salt of any of the above.

Another aspect of the present invention provides a pharmaceutical composition comprising either Compound 1, or a substantially pure diastereomer thereof; or Compound 2, or a substantially pure diastereomer thereof; or a pharmaceutically acceptable salt of any of the above, and a pharmaceutically acceptable carrier.

Another aspect of the present invention provides a method of treating a cancer which is T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, angiosarcoma, rhabdomyosarcoma, liposarcoma, malignant fibrous histiocytoma, hepatocellular carcinoma, intrahepatic and extrahepatic cholangiocarcinoma, and adenoid cystic carcinoma in a patient comprising administering to a patient in need thereof a therapeutically effective amount of Compound 1, a substantially pure diastereomer thereof, or a pharmaceutically acceptable salt thereof; or Compound 2, a substantially pure diastereomer thereof; or a pharmaceutically acceptable salt thereof.

A further aspect of the present invention provides a method of treating lung cancer in a patient comprising administering to a patient in need thereof a therapeutically effective amount of Compound 1, a substantially pure diastereomer thereof, or a pharmaceutically acceptable salt thereof, or Compound 2, a substantially pure diastereomer thereof, or a pharmaceutically acceptable salt thereof.

Another aspect of the present invention provides a method of treating sensorineural hearing loss caused by auditory hair cell loss in a patient in need thereof comprising administering a therapeutically effective amount of Compound 1, a substantially pure diastereomer thereof, or a pharmaceutically acceptable salt thereof; or Compound 2, a substantially pure diastereomer thereof, or a pharmaceutically acceptable salt thereof; to said patient.

A further aspect of the present invention provides a method of inducing auditory hair cell generation in a patient in need thereof, comprising administering a therapeutically effective amount of Compound 1, a substantially pure diastereomer thereof, or a pharmaceutically acceptable salt thereof, or Compound 2, a substantially pure diastereomer thereof, or a pharmaceutically acceptable salt thereof, to said patient.

Another aspect of the present invention provides Compound 1, a substantially pure diastereomer thereof, or a pharmaceutically acceptable salt thereof, or Compound 2, a substantially pure diastereomer thereof, or a pharmaceutically acceptable salt thereof, for use in therapy.

A further aspect of the present invention provides Compound 1, a substantially pure diastereomer thereof, or a pharmaceutically acceptable salt thereof, or Compound 2, a substantially pure diastereomer thereof, or a pharmaceutically acceptable salt thereof, for use in the treatment of T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, angiosarcoma, rhabdomyosarcoma, liposarcoma, malignant fibrous histiocytoma, hepatocellular carcinoma, intrahepatic or extrahepatic cholangiocarcinoma, or adenoid cystic carcinoma.

A still further aspect of the present invention provides Compound 1, a substantially pure diastereomer thereof, or a pharmaceutically acceptable salt thereof, or Compound 2, a substantially pure diastereomer thereof, or a pharmaceutically acceptable salt thereof, for use in the treatment of lung cancer.

A further aspect of the present invention provides Compound 1, a substantially pure diastereomer thereof, or a pharmaceutically acceptable salt thereof, or Compound 2, a substantially pure diastereomer thereof, or a pharmaceutically acceptable salt thereof for use in the treatment of sensorineural hearing loss caused by auditory hair cell loss.

A further aspect of the present invention provides Compound 1, a substantially pure diastereomer thereof, or a pharmaceutically acceptable salt thereof, or Compound 2, a substantially pure diastereomer thereof, or a pharmaceutically acceptable salt thereof, for use in inducing auditory hair cell generation.

Another aspect of the present invention provides use of Compound 1, a substantially pure diastereomer thereof, or a pharmaceutically acceptable salt thereof, or Compound 2, a substantially pure diastereomer thereof, or a pharmaceutically acceptable salt thereof, for the manufacture of a medicament fir the treatment of T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, angiosarcoma, rhabdomyosarcoma, liposarcoma, malignant fibrous histiocytoma, hepatocellular carcinoma, intrahepatic or extrahepatic cholangiocarcinoma, or adenoid cystic carcinoma.

A further aspect of the present invention provides use of Compound 1, a substantially pure diastereomer thereof, or a pharmaceutically acceptable salt thereof, or Compound 2, a substantially pure diastereomer thereof, or a pharmaceutically acceptable salt thereof, for the manufacture of a medicament for the treatment of lung cancer.

Another aspect of the present invention provides use of Compound 1, a substantially pure diastereomer thereof, or a pharmaceutically acceptable salt thereof, or Compound 2, a substantially pure diastereomer thereof, or a pharmaceutically acceptable salt thereof, for the manufacture of a medicament for the treatment of sensorineural hearing loss caused by auditory hair cell loss.

A further aspect of the present invention provides use of Compound 1, a substantially pure diastereomer thereof, or a pharmaceutically acceptable salt thereof, or Compound 2, a substantially pure diastereomer thereof, or a pharmaceutically acceptable salt thereof, for the manufacture of a medicament for inducing auditory hair cell generation.

A further aspect of the invention provides a method of treating sensorineural hearing loss caused by auditory hair cell loss in a canine companion animal comprising administering a therapeutically effective amount of Compound 1, a substantially pure diastereomer thereof, or a pharmaceutically acceptable salt thereof, or Compound 2, a substantially pure diastereomer thereof, or a pharmaceutically acceptable salt thereof, to said canine companion animal.

Another aspect of the invention provides a method of inducing auditory hair cell generation in a canine companion animal in need thereof, comprising administering a therapeutically effective amount of Compound 1, a substantially pure diastereomer thereof, or a pharmaceutically acceptable salt thereof, or Compound 2, a substantially pure diastereomer thereof, or a pharmaceutically acceptable salt thereof, to said canine companion animal.

The phrase "Compound 1, a diastereomer thereof" means 4,4,4-trifluoro-N-((2S)-1-((9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide; or a diastereomer 4,4,4-trifluoro-N-((S)-1-(((S)-9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide or 4,4,4-trifluoro-N-((S)-1-(((R)-9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide. Similarly, the phrase "Compound 2, a diastereomer thereof" means N-((2S)-1-((8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide; or a diastereomer N-((S)-1-(((S)-8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide or N-((S)-1-(((R)-8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide.

The term "patient" means mammal and "mammal" includes, but is not limited to, a human after the postnatal period. The postnatal period in a human is the period beginning immediately after childbirth and extending for 30 days.

"Therapeutically effective amount" or "effective amount" means the dosage of either Compound 1, a substantially pure diastereomer thereof, which is Isomer 1 or Isomer 2, or a pharmaceutically acceptable salt thereof, or Compound 2, a substantially pure diastereomer thereof, which is Isomer 1 or Isomer 2, or a pharmaceutically acceptable salt thereof, or pharmaceutical composition containing any of the above, necessary to inhibit Notch signaling in a cancer patient, and either destroy the target cancer cells or slow or arrest the progression of the cancer in a patient. Similarly, "therapeutically effective amount" or "effective amount" means the dosage of either Compound 1, a substantially pure diastereomer thereof, which is Isomer 1 or Isomer 2, or a pharmaceutically acceptable salt thereof, or Compound 2, a substantially pure diastereomer thereof, which is Isomer 1 or Isomer 2, or a pharmaceutically effective salt thereof, or a pharmaceutical composition containing any of the above, necessary to inhibit Notch signaling in a sensorineural hearing loss patient caused by auditory hair cell loss or damage, or induce auditory hair cell generation.

A "substantially pure diastereomer of Compound 1, or Compound 2" means Isomer 1 or Isomer 2 substantially free of the other Isomer. Compound 1 or Compound 2 is "substantially diastereomerically pure" when the isomeric purity at the 6-position of Compound 1 or the 5-position of Compound 2, is greater than 90% enantiomeric excess. In another embodiment, the isomeric purity is greater than 95% enantiomeric excess at the 6-position of Compound 1 or the 5-position of Compound 2. In still another embodiment, the isomeric purity is greater than 98% enantiomeric excess at the 6-position of Compound 1 or the 5-position of Compound 2. In yet another embodiment, the isomeric purity is greater than 99% enantiomeric excess at the 6-position of Compound 1 or the 5-position of Compound 2. All stereoisomers, including diastereomeric mixtures of Compound 1 or Compound 2 are contemplated within the present invention.

Anticipated dosages of Compound 1, a substantially pure diastereomer thereof, or a pharmaceutically acceptable salt thereof, or Compound 2, a substantially pure diastereomer thereof, or a pharmaceutically acceptable salt thereof, for treating cancer are in the range of 0.1 to 100 mg/patient/day. Preferred dosages are anticipated to be in the range of 1.0 to 75 mg/patient/day. Most preferred dosages are anticipated to be in the range of 2.0 to 50 mg/patient/day. Anticipated dosages of Compound 1, a diastereomer thereof, or a pharmaceutically acceptable salt thereof, or Compound 2, a diastereomer thereof, or a pharmaceutically acceptable salt thereof, for treating sensorineural hearing loss caused by auditory hair cell loss or damage, or induce auditory hair cell generation are in the range of 0.01 to 100 mg/patient/day. Preferred dosages are anticipated to be in the range of 0.1 to 10 mg/patient/day. Most preferred dosages are anticipated to be in the range of 0.2 to 1.0 mg/patient/day.

For cancer, sensorineural hearing loss, or inducing auditory hair cell generation, the exact dosage required to treat a patient and the length of treatment time will be determined by a physician in view of the stage and severity of the disease as well as the specific needs and response of the individual patient. Although expressed as dosage on a per day basis, the administration regimen may be adjusted to provide a more optimal therapeutic benefit to a patient and to manage and ameliorate any drug related toxicities. In addition to daily administration, administration every other day (Q2D); every other day over a five day period followed by two days without dosing (T.I.W.); every third day (Q3D); or once every week (Q.I.W.) over a 21-day dosing cycle; or other administration regimens may be appropriate.

The terms "treatment," "treat," and "treating," are meant to include the full spectrum of intervention for the cancer, sensorineural hearing loss caused by auditory hair cell loss or damage, or induction of auditory hair cell generation, such as administration of the active compound to alleviate, slow or reverse one or more of the symptoms and to delay progression of the cancer or auditory hair cell loss or damage from which the patient is suffering, or induce auditory hair cell generation in the patient.

"Canine companion animals" means domesticated and domestic-bred canines including, but not limited to, pets, service dogs, rescue dogs, herding dogs and livestock guardian dogs.

"Auditory hearing loss," "sensorineural hearing loss" or "hearing loss" in a human means the hearing threshold (softest sound heard (intensity) at a specific frequency) in a patient is 21 to 40 dB for mild; 41 to 55 dB for moderate; 56 to 70 dB for moderately-severe; 71 to 90 dB for severe; and 91 dB and above for profound. Intensities tested typically range from 0 dB up to 120 dB. Frequencies tested are typically 250, 500, 1000, 2000, 4000 and 8000 Hz. Diagnostic hearing evaluations are carried out by routine testing known and used by those skilled in the art including pure tone audiometry including pure tome average, speech audiometry including speech reception threshold, auditory brainstem response evaluations (ABR or BAER), transtympanic electrocochleography (ECOG), and otoacoustic emission testing (OAE). Pediatric and infant evaluations are also carried out by routine testing known and used by those skilled in the art including visual reinforcement audiometry, play audiometry, otoacoustic emissions (OAEs), and auditory brainstem response evaluations.

A compound of the present invention is preferably formulated as a pharmaceutical composition with a pharmaceutically acceptable carrier and administered by a variety of routes. Preferably, for treating cancer, such compositions are for oral administration.

For treating sensorineural hearing loss cause by auditory hair cell loss or damage, or inducing auditory hair cell generation a pharmaceutical composition suitable for oral or parenteral administration to afford local or systemic therapy may be formulated and administered. Oral compositions include tablets, coated tablets, hard or soft gelatin capsules, solutions, emulsions or suspensions. Parenteral compositions may be formulated to permit administration including subcutaneous injections, intravenous, intramuscular intraperitoneal, intrapleural, intrasternal, transtympanic, intralabryinthine, or intracochlear injections, or infusion. The pharmaceutical compositions may be formulated to permit a compound of the invention to be bioavailable upon administration of the composition to a patient, or formulated to afford controlled or sustained release of the active pharmaceutical ingredient. A pharmaceutical composition suitable for transtympanic administration to the middle ear cavity is preferred, and administration to the round window niche of the middle ear is also preferred. Intralabryrinthine injection and intracochlear injection are also contemplated. The preferred route of administration for hearing loss treatment is local transtympanic injection, however this does not exclude pharmaceutical compositions suitable for alternate routes of administration to afford systemic delivery and may include compositions and dosing regimes alternative or in addition to local transtympanic administration. Also preferred is a sustained release local delivery composition where the release interval may range from three (3) days to ninety (90) days depending on the delivery vehicle, or mixture of delivery vehicle agents, in which Compound 1, or a substantially pure diastereomer, or a pharmaceutically acceptable salt thereof, is associated.

Pharmaceutical compositions, processes for preparing, and delivery systems for targeted delivery of drugs are well known in the art. See, e.g., REMINGTON: THE SCIENCE AND PRACTICE OF PHARMACY (A. Gennaro, et al., eds., 19$^{th}$ ed., Mack Publishing Co., 1995); Salt and Plontke, "Principles of Local Drug Delivery to the Inner Ear", *Audiol Neurotol*, 2009, (14); 350-360; Rhee, et al., "Sustained-Release Injectable Drug Delivery," *Pharmaceutical Technology*, Special Issue Drug Delivery, 1 Nov. 2010. The pharmaceutical compositions may contain preservatives, solubilizers, stabilizers, wetting agents, emulsifiers, sweeteners, colorants, flavorants, salts for varying osmotic pressure, buffers, masking agents, or antioxidants.

A compound of the present invention is capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Compound 1, a substantially pure diastereomer thereof, or a pharmaceutically acceptable salt thereof, or Compound 2, a substantially pure diastereomer thereof, or a pharmaceutically acceptable salt thereof, may be prepared by a variety of procedures known in the art, as well as those described below. The specific synthetic steps may be combined in different ways to prepare Compound 1, a diastereomer thereof, or a pharmaceutically acceptable salt thereof, or Compound 2, a diastereomer thereof, or a pharmaceutically acceptable salt thereof.

Compound 1 is named: 4,4,4-trifluoro-N-((2S)-1-((9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide and may also be named 4,4,4-trifluoro-N-{(1S)-2-[(9-methoxy-3,3-dimethyl-5-oxo-2,3,5,6-tetrahydro-1H-pyrrolo[1,2-a][1]benzazepin-6-yl)amino]-1-methyl-2-oxoethyl}butanamide; and may also be named: butanamide, 4,4,4-trifluoro-N-[(1S)-1-methyl-2-oxo-2-[(2,3,5,6-tetrahydro-9-methoxy-3,3-dimethyl-5-oxo-1H-pyrrolo[1,2-a][1]benzazepin-6-yl)amino]ethyl]-; and other names may be used to unambiguously identify Compound 1. The diastereomers are named 4,4,4-trifluoro-N-((S)-1-(((S)-9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide and 4,4,4-trifluoro-N-((S)-1-(((R)-9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide. Other names may be used to unambiguously identify each of the diastereomers.

Compound 2 is named: N-((2S)-1-(8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide and may also be named N-{(1S)-2-[(8,8-dimethyl-6-oxo-6,8,9,10-tetrahydro-5H-pyrido[3,2-f]pyrrolo[1,2-a]azepin-5-yl)amino]-1-methyl-2-oxoethyl}-4,4,4-trifluorobutanamide; and may also be named: butanamide, 4,4,4-trifluoro-N-[(1S)-1-methyl-2-oxo-2-[(6,8,9,10-tetrahydro-8,8-dimethyl-6-oxo-5H-pyrido[3,2-f]pyrrolo[1,2-a]azepin-5-yl)amino]ethyl]-; and other names may be used to unambiguously identify Compound 2. The diastereomers are named N-((S)-1-(((S)-8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide and N-((S)-1-(((R)-8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide. Other names may be used to unambiguously identify each of the diastereomers.

It will be understood Compound 1 and Compound 2 are depicted with one of two chiral centers fixed. Herein, the Cahn-Ingold-Prelog designations of (R)- and (S)- are used to refer to specific isomers. Specific stereoisomers can be prepared by stereospecific synthesis using enantiomerically pure or enriched starting materials. The specific stereoisomers of either starting materials, intermediates, or racemic mixtures including Compound 1 or Compound 2 can be resolved by techniques well known in the art, such as those found in *Stereochemistry of Organic Compounds*, E. I. Eliel and S. H. Wilen (Wiley 1994) and *Enantiomers, Racemates, and Resolutions*. J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. Where a chiral compound is isolated or resolved into its isomers, but absolute configurations or optical rotations are not determined, the isomers are arbitrarily designated as Isomer 1 and Isomer 2 corresponding to the order each elutes from chiral chromatography and if chiral chromatography is initiated early in the synthesis, the same designation is applied to subsequent intermediates and examples. While all mixtures containing the compounds of the present invention are contemplated within the present invention, the preferred embodiment is Compound 1, Isomer 2, or Compound 2, Isomer 2.

The compounds employed as initial starting materials in the synthesis of the compounds of the present invention are well known and, to the extent not commercially available, are readily synthesized using specific references provided, by standard procedures commonly employed by those of ordinary skill in the art or are found in general reference texts.

Examples of known procedures and methods include those described in general reference texts such as Comprehensive Organic Transformations, VCFI Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

As used herein, the following terms have the meanings indicated: "mAtoh1" refers to murine atonal homolog 1 protein; "hAtoh 1 refers to human atonal homolog 1 protein; "Atoh1" refers to the human gene atonal homolog 1; "Basic Medium" refers to 500 ml DMEM/F12 medium+5 ml N2 100× stock and 10 ml B27 50× stock plus 500 µl Ampicillin stock (1000×, 50 mg/ml) and 1.667 µl Fungizone (300×); "BFGF" refers to basic fibroblast growth factor; "DMEM" refers to Dulbecco's Modified. Eagle's Medium; "DMSO" refers to dimethylsulfoxide; "EDTA" refers to ethylenediaminetetraacetic acid; "EGF" refers to epidermal growth factor; "EGTA" refers to ethylene glycol-bis(2-aminoethylether)-N,N,N',N'-tetra acetic acid; ES/MS refers to electrospray mass spectroscopy; "FBS" refers to fetal bovine serum; "GFP" regers to green fluorescent protein; "h" refers to hour or hours; "HBSS" refers to Hank's Balanced Salt Solution; "HEK" refers to human embryonic kidney; "IC$_{50}$" refers to the concentration of an agent that produces 50% of the maximal inhibitory response possible for that agent; "IgG" refers to immunoglobulin G; "MathI" refers to the human gene atonal homolog 1; "Medium A" refers to 200 ml Basic medium+EGF bFGF+IGF-1+Heparan Sulfate at 20, 10, 50, and 50 ng/ml respectively; "MEM" refers to minimum essential medium; "min" refers to minutes; "MS" refers to mass spectroscopy; "N1ICD" refers to Notch1 Intracellular Domain; "nGFP" refers to nuclear green fluorescent protein; "OC" refers to organ of corti; "PBS" refers to phosphate buffered saline; "PBST" refers to Phosphate Buffered Saline+Tween®; "qPCR" refers to quantitative polymerase chain reaction; "qRT-PCR" refers to quantitative reverse transcription polymerase chain reaction; "rpm" refers to revolutions per minute; "RLT buffer" refers to RNeasyLysis buffer; "RT" refers to room temperature; "Tbp" refers to TATA-binding protein;

Preparation 1

1-Bromo-3-(2-bromo-4-methoxy-phenyl)propan-2-one

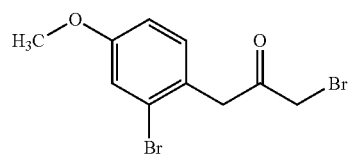

Add trimethylsilyldiazomethane (118.4 mL, 236.80 mmol, 2M in hexanes) dropwise to a stirred 0° C. solution of 2-(2-bromo-4-methoxy-phenyl)acetyl chloride (52 g, 197.3 mmol) in tetrahydrofuran (197 mL) and acetonitrile (197 mL) under nitrogen. After 15 minutes allow to warm to RT and stir for 2 h under nitrogen. Concentrate to obtain a thick red oil (61 g). Add hydrogen bromide (36 mL, 197 mmol, 33% in acetic acid) dropwise to a stirred 5° C. solution of 2-(2-bromo-4-methoxy-phenyl)acetyl azide from previous step in acetic acid (265 mL). After addition, allow to warm to RT under nitrogen. After 45 minutes, quench with ice/water, (500 mL) resulting in a brown precipitate. Filter solids and wash with water (100 mL) and hexanes (100 ml) and dry under vacuum at 45° C. for 2 h to yield the title compound as an orange oil (63.0 g, 99%). 1H NMR (300 MHz, CDCl$_3$): 7.17-7.12 (m, 2H), 6.85 (dd, J=2.5, 8.5 Hz, 1H), 4.03 (s, 2H), 3.97 (s, 2H), 3.79 (s, 3H).

Preparation 2

(3Z)-1-(2-Bromo-4-methoxy-phenyl)-3-(3,3-dimethylpyrrolidin-2-ylidene)propan-2-one

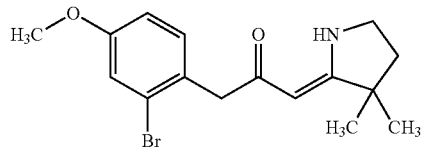 [SMILES: COc1ccc(CC(=O)/C=C2\NCCC2(C)C)c(Br)c1]

Add 3,3-dimethylpyrrolidine-2-thione (26.5 g, 205 mmol) to a suspension of the intermediate provided by Preparation 1,1-bromo-3-(2-bromo-4-methoxy-phenyl)propan-2-one (60.00 g, 186 mmol), and potassium iodide (31 g, 86 mmol) in tetrahydrofuran (600 mL) at RT in one portion and stir for 1 h. Add methyl tert-butyl ether (200 mL), filter out solids and rinse filter cake with methyl-tert-butyl ether (100 mL) to afford 1-(2-bromo-4-methoxy-phenyl)-3-[(4,4-dimethyl-2,3-dihydropyrrol-1-ium-5-yl)sulfanyl]propan-2-one iodide as a light yellow solid (100 g). To a suspension of the solid (100 g, 201 mmol) in acetonitrile (1 L), add triethylamine (56 mL, 401 mmoles) and triphenylphosphine (58 g, 221 mmol) and stir at 65° C. for 2.5 h. Add methyl tert-butyl ether (200 ml) and filter out solids. Evaporate filtrate, triturate residue with methyl tert-butyl ether (20 mL) and filter out solids (twice). Evaporate combined filtrates to obtain 50 g crude material. Purify the residue via flash column chromatography on silica eluting with a 20-50% gradient of ethyl acetate in hexanes to obtain the title compound as an off-white solid (41 g, 70%). MS (m/z): 338.0/340.0 (M+/M+2).

Preparation 3

9-Methoxy-3,3-dimethyl-2,3-dihydro-1H-pyrrolo[1,2-A][1]benzazepin-5(6H)-one

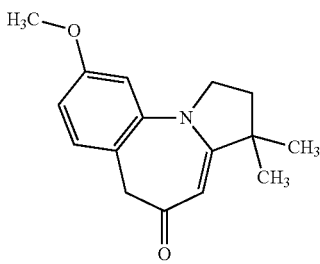

Degas/flush with nitrogen (×3) a mixture of the intermediate provided by Preparation 2, (3Z)-1-(2-bromo-4-methoxy-phenyl)-3-(3,3-dimethylpyrrolidin-2-ylidene)propan-2-one (40.0 g, 118 mmol), palladium acetate (2.7 g, 12 mmol), cesium carbonate (77 g, 237 mmol), 4,5-bis(diphenylphosphino)-9,9-dimethylxanthene (13.7 g, 24 mmol), and N-methyl-2-pyrrolidone (1.2 L). Heat the suspension at 150° C. for 4 h. Cool to RT, filter off solids, wash with ethyl acetate and discard solids. Add ethyl acetate (1 L) and water (500 mL) to the filtrate, filter off solids through diatomaceous earth and discard. Separate filtrate layers, extract from aqueous with ethyl acetate (2×20 mL), followed by dichloromethane (3×100 mL). Wash combined organic layers with 5% aqueous sodium bicarbonate solution twice, dry over sodium sulfate, filter and concentrate to obtain 100 mL dark brown oil. Filter material over a silica pad eluting with dichloromethane followed by 1% methanol/dichloromethane and concentrate filtrate. Partition residue between ethyl acetate and 5% aqueous sodium bicarbonate solution, back-extract from aqueous with ethyl acetate, dry over sodium sulfate, filter and concentrate to obtain crude product as a dark brown foam. Dissolve resulting foam in ethyl acetate (250 mL), add SiliaBond Thiol® (80 g) and stir at RT overnight. Filter out solids, wash filter cake with ethyl acetate and dichloromethane, concentrate filtrate to obtain the title compound as a light brown solid (19.6 g, 65%). MS (m/z): 258.0 (M+H).

Preparation 4

6-Hydroxyimino-9-methoxy-3,3-dimethyl-2,3-dihydro-1H-pyrrolo[1,2-a][1]benzazepin-5(6H)-one

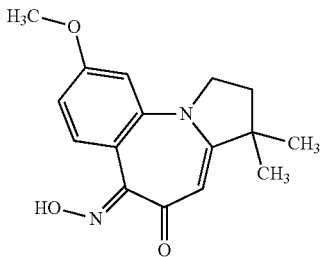

Add potassium tert-butoxide (11 g, 98 mmol) in several portions to a stirred 0° C. solution of the intermediate provided by Preparation 3, 9-methoxy-3,3-dimethyl-2,3-dihydro-1H-pyrrolo[1,2-A][1]benzazepin-5(6H)-one (16.8 g, 65 mmol), in tetrahydrofuran (336 mL) and stir for 15 minutes. Add amyl nitrite (12.2 mL, 91 mmol) dropwise and stir mixture for 30 minutes at 0° C. Pour reaction mixture onto ice/water (200 mL) and extract the mixture with ethyl acetate (2×200 mL). Filter out crystallized solids, extract from filtrate with dichloromethane (2×100 mL). Wash combined organics with brine (100 mL), dry over sodium sulfate, filter and concentrate to afford a light brown solid. Triturate solid with 1:1 methyl tert-butyl ether/hexane, combine with previously collected solid to obtain the title compound as a light yellow solid (16.5 g, 88%). MS (m/z): 287.1 (M+H).

Preparation 5

6-Amino-9-methoxy-3,3-dimethyl-2,3-dihydro-1H-pyrrolo[1,2-a][1]benzazepin-5(6H)-one

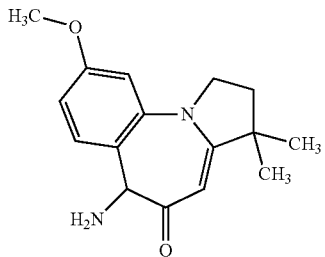

Add trifluoroacetic acid (17 mL, 231 mmol) dropwise over 10 minutes to a stirred 5° C.-10° C. suspension of the intermediate provided by Preparation 4, 6-hydroxyimino-9-methoxy-3,3-dimethyl-2,3-dihydro-1H-pyrrolo[1,2-a][1]benzazepin-5(6H)-one (16.5 g, 58 mmol), and zinc dust (11.3 g, 173 mmol) in dichloromethane (248 mL) then allow to warm to RT. Filter mixture through a pad of diatomaceous earth, pour filtrate over a mixture of ice and saturated aqueous sodium carbonate (1:1, 500 mL). Filter the resulting suspension through diatomaceous earth and rinse filter pad with dichloromethane. Extract from aqueous layer with dichloromethane (100 mL), dry combined organic layers over sodium sulfate, filter and concentrate to obtain the title compound as a light brown foam (14.7 g, 94%). MS (m/z): 273.1 (M+H).

Preparation 6

Benzyl (2S)-2-(4,4,4-trifluorobutanoylamino)propanoate

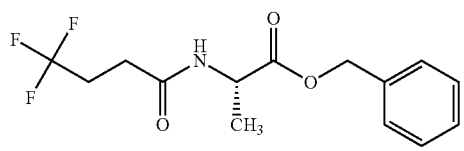 [SMILES: C[C@H](NC(=O)CCC(F)(F)F)C(=O)OCc1ccccc1]

Add L-alanine benzyl ester hydrochloride (7 g, 32.5 mmol), diisopropylethylamine (28 mL, 162 mmol), hydroxybenzotriazole hydrate (7.5 g, 49 mmol), and 1-(3- dimethylaminopropyl)-3-ethylcarbodiimide hydrochloride (9.3 g, 49 mmol) to a stirred solution of 4,4,4-trifluorobutyric acid (7.1 g, 49 mmol) in dichloromethane (162 mL) and stir at RT under $N_2$ for 20 h. Quench with 20% aqueous citric acid solution (150 mL), stir mixture for 5 minutes, separate layers and extract from aqueous with dichloromethane (100 mL). Wash combined organic layers with saturated aqueous sodium bicarbonate solution (150 mL), dry over magnesium sulfate, filter and concentrate to obtain 10.6 g pale yellow solid. Purify the residue via flash column chromatography on silica eluting with a 25-50% gradient of ethyl acetate in hexanes to obtain the title compound as a white solid (9.2 g, 94%). MS (m/z): 304.2 (M+H).

Preparation 7

(2S)-2-(4,4,4-trifluorobutanoylamino)propanoic acid

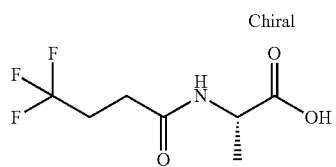

Add palladium (1.8 g, 0.8 mmol, 5% on C) to a stirred solution of the intermediate provided by Preparation 6, benzyl (2S)-2-(4,4,4-trifluorobutanoylamino)propanoate (8.8 g, 29 mmol), in methanol (88 mL) at RT. Degas the mixture and stir under hydrogen (balloon atmosphere) for 5 h. Filter the mixture over diatomaceous earth, wash pad with methanol and concentrate filtrate to obtain a white solid. Triturate solids with dichloromethane and dry under vacuum overnight at RT to yield the title compound as a white solid (6.11 g, 99% yield). MS (m/z): 214.1 (M+H).

Preparation 8

Methyl 3-(3,3-dimethyl-2-thioxopyrrolidin-1-yl)propanoate

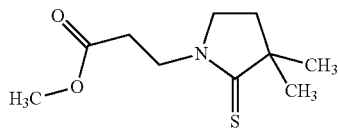

Dissolve 3,3-dimethylpyrrolidine-2-thione (15.7 g, 122 mmol) and methyl acrylate (12 mL, 134 mmol) in tetrahydrofuran (100 mL) and stir at RT under nitrogen. Add sodium hydroxide (0.8 g, 20 mmol) and stir overnight at RT under nitrogen. Dilute with brine, extract with ethyl acetate, separate layers, wash the organic layer with brine, dry over sodium sulfate, filter and concentrate to yield 27.5 g crude solids. Purify the residue via flash column chromatography on silica eluting with a 20-50% gradient of ethyl acetate in hexanes to obtain the title compound as a white solid (25.9 g, 99%). MS (m/z): 216.2 (M+H).

Preparation 9

Methyl 3-[(2Z)-2-(2-ethoxy-2-oxo-ethylidene)-3,3-dimethyl-pyrrolidin-1-yl]propanoate

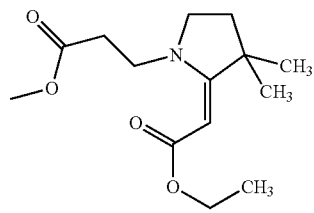

Add tetrakis(acetato)dirhodium(II) (3.74 g, 8.5 mmol) to a stirred solution of the intermediate provided by Preparation 8, methyl 3-(3,3-dimethyl-2-thioxopyrrolidin-1-yl)propanoate (41.4 g, 192 mmol), in toluene (156 mL) and heat to 110° C. under nitrogen. Add ethyldiazoacetate (89 mL, 844 mmol) dropwise over approximately 18 h then heat overnight at 110° C. Concentrate and purify the residue via flash column chromatography on silica eluting with 30% ethyl acetate in hexanes to obtain the title compound as a yellow oil (34.5 g, 67%). MS (m/z): 270.2 (M+H).

Preparation 10

Ethyl (2Z)-2-(3,3-dimethylpyrrolidin-2-ylidene)acetate

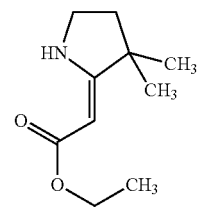

Add potassium hexamethyldisilazide (301 mL, 0.5 M in toluene, 151 mmol) dropwise over 45 minutes to a stirred solution of the intermediate provided by Preparation 9, methyl 3-[(2Z)-2-(2-ethoxy-2-oxo-ethylidene)-3,3-dimethyl-pyrrolidin-1-yl]propanoate (33.8 g, 126 mmol), in tetrahydrofuran (430 mL) under nitrogen using a water/ice bath to maintain temperature <30° C. Stir for 40 minutes after completion of addition. Quench with saturated aqueous sodium bicarbonate solution (250 mL) then concentrate. Partition between diethyl ether and brine solution, extract from aqueous with ethyl acetate (×4), dry over sodium sulfate, filter and concentrate to obtain 37 g material. Purify the residue via flash column chromatography on silica eluting with 10% ethyl acetate in hexanes to obtain the title compound (9.1 g, 40%). MS (m/z): 184.2 (M+H).

Preparation 11

Ethyl (2 Z)-2-[3,3-dimethyl-1-(3-methyl-2-pyridyl)pyrrolidin-2-ylidene]acetate

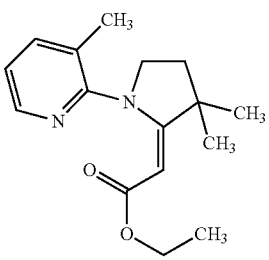 [SMILES: CCOC(=O)/C=C1\N(c2ncccc2C)CCC1(C)C]

Combine 2-bromo-3-methylpyridine (1.5 g, 8.7 mmol), the intermediate provided by Preparation 10, ethyl (2Z)-2-(3,3-dimethylpyrrolidin-2-ylidene)acetate (1.6 g, 8.7 mmol), and sym-dimethylethylene diamine (0.77 mL, 8.7 mmol) in 1,4-dioxane (15 mL) in a reaction vessel. Bubble nitrogen through the solution with stirring for 10 minutes. Add potassium carbonate (3.6 g, 26 mmol) and copper (I) iodide (0.83 g, 4.4 mmol) all at once, seal and heat stirred mixture at 120° C. for 2 days. Dilute with dichloromethane, filter through diatomaceous earth and concentrate filtrate. Purify the residue via flash column chromatography on silica eluting with a gradient of 5-100% ethyl acetate in hexanes to obtain the title compound as a pale yellow oil (1.58 g, 66%). MS (m/z): 275.0 (M+H).

Preparation 12

8,8-Dimethyl-9,10-dihydro-5H-pyrido[3,2-f]pyrrolo[1,2-a]azepin-6(8H)-one

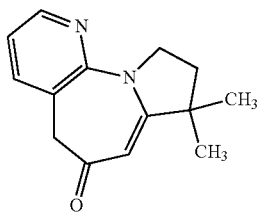 [SMILES: CC1(C)CCN2C1=CC(=O)Cc1cccnc12]

Add sodium bis(trimethylsilyl)amide (22 mL, 1M in tetrahydrofuran, 22 mmol) via syringe to a stirred solution of the intermediate provided by Preparation 11, ethyl (2Z)-2-[3,3-dimethyl-1-(3-methyl-2-pyridyl)pyrrolidin-2-ylidene]acetate (2.88 g, 10.5 mmol), and tetrahydrofuran (60 mL) in a reaction vessel. Seal vessel and heat at 70° C. with stirring for 3 days. Cool to RT, quench with brine, extract with ethyl acetate, dry over sodium sulfate, filter and concentrate to obtain a brown oil. Purify the residue via flash column chromatography on silica eluting with a gradient of 50-100% ethyl acetate in hexanes to obtain the title compound as a yellow solid (130 g, 71%). MS (m/z): 229.2 (M+H).

Preparation 13

6-Azido-10-aza-3,3-dimethyl-2,6-dihydro-1H-pyrrolo[1,2-a][1]benzazepin-5-one

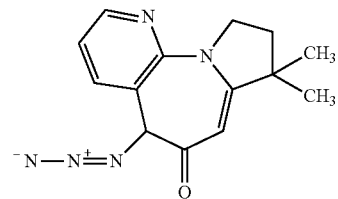 [SMILES: CC1(C)CCN2C1=CC(=O)C(N=NN)c1cccnc12]

Add lithium diisopropylamide (7.0 mL, 10.5 mmol, 1.5 M in hexanes) over 10 minutes to a stirred −78° C. solution of the intermediate provided by Preparation 12, 8,8-dimethyl-9,10-dihydro-5H-pyrido[3,2-f]pyrrolo[1,2-a]azepin-6(8H)-one (1.85 g, 8.1 mmol), in tetrahydrofuran (50 mL) under nitrogen. After 30 minutes add acetic acid (2.3 mL, 41 mmol) via syringe then allow to warm to RT under nitrogen. Quench with saturated aqueous sodium bicarbonate solution. Partition mixture between brine and ethyl acetate, separate layers, wash ethyl acetate layer with brine, dry over sodium sulfate, filter and concentrate to obtain a brown solid. Purify the residue via flash column chromatography on silica eluting with a gradient of 5-60% ethyl acetate in hexanes to obtain the title compound (1.2 g, 55%). MS (m/z): 270.2 (M+H).

Preparation 14

5-Amino-3,3-dimethyl-9,10-dihydro-5H-pyrido[3,2-f]pyrrolo[1,2-a]azepin-6(8H)-one

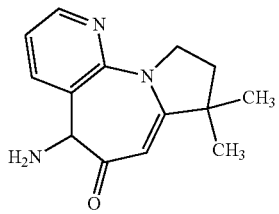 [SMILES: CC1(C)CCN2C1=CC(=O)C(N)c1cccnc12]

Add zinc dust (1.2 g, 18 mmol) followed by ammonium chloride (5 g, 66 mmol) to a stirred solution of the intermediate provided by Preparation 13, 6-azido-10-aza-3,3-dimethyl-2,6-dihydro-1H-pyrrolo[1,2-a][1]benzazepin-5-one (1.2 g, 4.5 mmol), in ethanol (50 mL) and water (15 mL) at RT. After 1 h dilute with ethyl acetate, filter out solids and concentrate filtrate. Suspend residue between ethyl acetate and brine, separate layers, dry over sodium sulfate, filter and concentrate. Purify the residue via flash column chromatography on silica eluting with a gradient of a 5-40% [10% 2M ammonia in methanol/dichloromethane] in dichloromethane to obtain the title compound as a yellow solid (0.72 g, 67%). MS (m/z): 244.2 (M+H).

Preparation 15 tert-Butyl N-[(1S)-2-[(10-aza-3,3-dimethyl-5-oxo-2,6-dihydro-1H-pyrrolo[1,2-a][1]benzazepin-6-yl)amino]-1-methyl-2-oxo-ethyl]carbamate

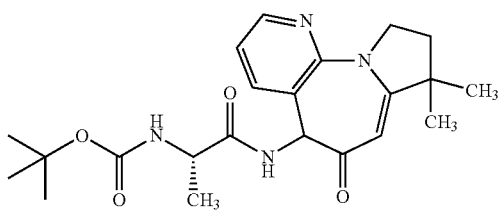 [SMILES: C[C@H](NC(=O)OC(C)(C)C)C(=O)NC1C(=O)C=C2N(CCC2(C)C)c2ncccc21]

Add (2S)-2-(tert-butoxycarbonylamino)propanoic acid (0.69 g, 3.6 mmol), 1-hydroxybenzotriazole hydrate (0.55 g, 3.6 mmol) and diisopropylethylamine (0.67 mL, 3.9 mmol) to a stirred 0° C. solution of the intermediate provided by Preparation 14, 5-amino-3,3-dimethyl-9,10-dihydro-5H-pyrido[3,2-f]pyrrolo[1,2-a]azepin-6(8H)-one (0.72 g, 3.0 mmol), in tetrahydrofuran (10 mL) under nitrogen. Add 1-(3-dimethylaminopropyl)-3-ethylcarbodiimide hydrochloride (0.68 g, 3.6 mmol) and allow mixture to warm to RT under nitrogen. After 2 h, dilute with water and extract with ethyl acetate. Wash organic layer with brine, dry over sodium sulfate, filter and concentrate. Purify the residue via flash column chromatography on silica eluting with a gradient of 50-100% ethyl acetate in hexanes to obtain the title compound as a yellow solid (1.04 g, 84%). MS (m/z): 415.0 (M+H).

Preparation 16

(2S)-2-Amino-N-(10-aza-3,3-dimethyl-5-oxo-2,6-dihydro-1H-pyrrolo[1,2-a][1]benzazepin-6-yl)propanamide hydrochloride

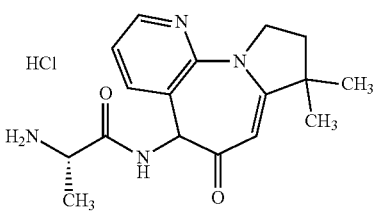 [SMILES: C[C@H](N)C(=O)NC1C(=O)C=C2N(CCC2(C)C)c2ncccc21 ; Cl]

Add hydrogen chloride (12.5 mL, 50 mmol, 4M in dioxane) to a stirred solution of the intermediate provided by Preparation 15 tert-butyl N-[(1S)-2-[(10-aza-3,3-dimethyl-5-oxo-2,6-dihydro-1H-pyrrolo[1,2-a][1]benzazepin-6-yl)amino]-1-methyl-2-oxo-ethyl] carbamate (1.04 g, 2.5 mmol), in 1,4-dioxane (40 mL) and warm to 45° C. with stirring. When LC/MS indicates complete reaction, concentrate to obtain the title compound as a yellow solid (0.93 g, crude). MS (m/z): 315.2 (M+1).

EXAMPLE 1

4,4,4-trifluoro-N-((2S)-1-(9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide

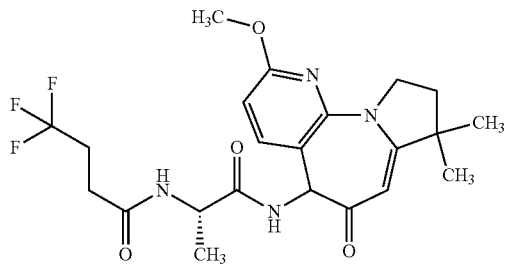 [SMILES: COc1ccc2c(n1)N1CCC(C)(C)C1=CC(=O)C2NC(=O)[C@H](C)NC(=O)CCC(F)(F)F]

Part 1

Diastereomeric 4,4,4-trifluoro-N-((2S)-1-((9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide Add 1-(3-dimethylaminopropyl)-3-ethylcarbodiimide hydrochloride (12.4 g, 65 mmol) to a stirred solution of the intermediate provided by Preparation 5, 6-Amino-9-methoxy-3,3-dimethyl-2,3-dihydro-1H-pyrrolo[1,2-a][1]benzazepin-5(6H)-one, and the intermediate provided by Preparation 7, (2S)-2-(4,4,4-trifluorobutanoylamino)propanoic acid (10.9 g, 51 mmol), in dichloromethane (294 mL) at RT. Cool mixture to 5° C., add 1-hydroxybenzotriazole (8.75 g, 65 mmol) and continue stirring at RT for 10 minutes. Wash mixture with water (3×100 mL), dry over sodium sulfate, filter and concentrate to afford a dark solid. Triturate with methyl tert-butyl ether to afford the title compound (mixture of diastereomers) as an off-white solid (22.0 g, 87%). MS (m/z): 468.1 (M+H).

Part 2

4,4,4-trifluoro-N-((2S)-((9-methoxy-3,3-dimethyl-5-oxo-2,3,5,6-tetrahydro-1H-benzo[f]pyrrolo[1,2-a]azepin-6-yl)amino)-1-oxopropan-2-yl)butanamide Isomers 1 and 2

Separate a mixture of diastereomers from Example 1, Part 1 on a Chiralpak AD column eluting with 10% acetonitrile/ethanol (0.2% dimethylethylamine) to obtain Isomer 1 compound ($R_t$=3.20 mins.) as a white solid (9.8 g, 38%) and Isomer 2 compound (Rt=7.37 mins.) as a white solid (9.0 g, 36% MS (m/z): 468.2 (M+H) for both isomers.

EXAMPLE 2

N-((2S)-1-((8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide

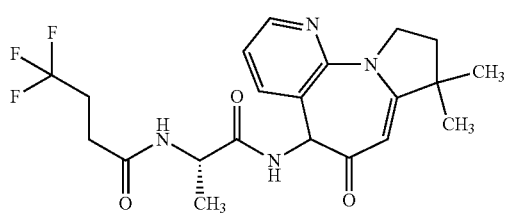 [SMILES: C[C@H](NC(=O)CCC(F)(F)F)C(=O)NC1C(=O)C=C2N(CCC2(C)C)c2ncccc21]

Part 1

Diastereomeric N-{(1S)-2-[(8,8-Dimethyl-6-oxo-6,8,9,10-tetrahydro-5H-pyrido[3,2-f]pyrrolo[1,2-a]azepin-5-yl)amino]-1-methyl-2-oxoethyl}-4,4,4-trifluorobutanamide Add 4,4,4-trifluorobutanoic acid (0.45 g, 3.2 mmol), 1-hydroxybenzotriazole hydrate (0.49 g, 3.2 mmol) and diisopropylethylamine (2.3 mL, 13.2 mmol) to a stirred 0° C. solution of the intermediate provided by Preparation 16, (2S)-2-amino-N-(10-aza-3,3-dimethyl-5-oxo-2,6-dihydro-1H-pyrrolo[1,2-a][1]benzazepin-6-yl)propanamide hydrochloride (0.93 g, 2.6 mmol), in tetrahydrofuran (50 mL) under nitrogen. Add 1-(3-dimethylaminopropyl)-3-ethylcarbodiimide hydrochloride (0.61 g, 3.2 mmol) and allow mixture to warm to RT under nitrogen for 16 h. Dilute with water and extract with ethyl acetate. Wash organic layer with brine, dry over sodium sulfate, filter and concentrate. Purify the residue via flash column chromatography on silica eluting with a gradient of 75-100% ethyl acetate in hexanes to obtain title compound (mixture of diastereomers) as an off-white solid (0.82 g, 71%). MS (m/z): 439.2 (M+1).

Part 2

N-((2S)-1-((8,8-dimethyl-6-oxo-6,8,9,10-tetrahydro-5H-pyrido[3,2-f]pyrrolo[1,2-a]azepin-5-yl)amino)-1-oxopropan-2-yl)-4,4,4-trifluorobutanamide Isomers 1 and 2

Separate a mixture of diastereomers from Example 2, Part 1 on a Chiralpak AD-H column eluting with 15% MeOH/$CO_{2(gas)}$ to obtain Isomer 1 ($R_t$=1.60 mins.) as a white solid (194 mg, 24%, epimerizes to 32% DE (diastereomeric excess)) and Isomer 2 ($R_t$=2.31 mins.) as a white solid (469 mg, 57%). MS (m/z): 439.0 (M+H) for both isomers.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenviroments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Miteiman Database of Chromosome Aberrations in Cancer at the US National Cancer Institute (NCI) Cancer Genome Anatomy Project (CLAP). The database includes chromosomal aberrations for at least some of the malignancies of the present invention. The Wellcome Trust Sanger Institute Cancer Genome Project maintains a detailed online "Cancer Gene Census" of all human genes that have been causally linked to tumorigenesis as well as the COSMIC (Catalogue of Somatic Mutations in Cancer) database of somatic mutations in human cancer. A further source containing abundant information on cytogenetic changes causally linked to various cancers is the Atlas of Genetics and Cytogenetics in Oncology and Haematology.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

The oncogenic role of Notch was first reported in human T-cell leukemia involving a translocation of the Notch1 intracellular domain to the T-cell receptor-β promoter region, resulting in the over expression of Notch1 intracellular domain (Grabber et al. *Nature Review Cancer*, 2006 (6)347-359; Weng et al. *Science*, 2004(306):269-271). Over expression of Notch1 intracellular domain in hematopoietic progenitor cells of mice caused the mice to exhibit T-cell acute lymphoblastic leukemia similar to humans. In addition to T-cell acute lymphoblastic leukemia, there is increasing evidence that Notch signals are oncogenic in other cancers through multiple mechanisms including receptor amplification and over expression of ligands and/or receptors including acute lymphoblastic leukemia, chronic lymphoblastic leukemia (Rosati et al, *Blood*, 2009(113): 856-865), acute myelogenous leukemia (Sliwa et al. *Int J Clin Exp Pathol*, 2014(7(3)); 882-889), chronic myelogenous leukemia (Nakahara et al. *Blood*, 2010(115(14)): 2872-2881), and erythroleukemia (Robert-Moreno et al, *Leukemia*, 2007(21): 1496-1503). Aberrant constitutive Notch signaling due to mutation or over expression of ligands and/or receptors is also implicated in a number of solid tumor malignancies including triple negative breast cancer (Stoerk et al, *Cancer Discovery*, 2014(4): 1154-1167), breast cancer, ovarian cancer (Park et al. *Cancer Research*, 2006(66):6312-6318), melanoma (Gast et al. *Genes, Chromosomes & Cancer*, 2010(49):733-745), lung cancer, non small cell lung cancer (Westhoff et al. *PNAS*, 2009(106):22293-22298), pancreatic cancer, glioblastoma, colorectal cancer, head and neck cancer, cervical cancer, prostate cancer, liver cancer, squamous cell carcinoma (oral), skin cancer and medulloblastoma (Rangathan et al., *Nature Review Cancer.* 2011(11):338-351 and Supplementary information S1 (table)). Aberrant constitutive Notch signaling due to mutation or over expression of ligands and/or receptors is also implicated in angiosarcoma (Ravi et al, *J Clin Oncol*, 2007, (25(18S, June 20 Supplement)): Abstract 10030), rhabdomyosarcoma (Belyea et al, *Clin Cancer Res*, 2011(17(23)): 7324-7336; Roma et al, *Clin Cancer Res*, 2011(17(3)): 505-513), liposarcoma (*J Clin Oncol*, 2009, (27(15S, Supplement)): Abstract 10526), malignant fibrous histiocytoma (Wang et al, *Cancer Res*, 2012, (72): 1013-1022), hepatocellular carcinoma (Villanueva et al, *Gastroenterology*, 2012, (143): 1660-1669), intrahepatic and extrahepatic cholangiocarcinoma (Wu et al, *Int J Exp Pathol*, 2014, (7(6)): 3272-3279; Sekiya et al, *J Clin Invest*, 2012, (122(11)): 3914-3918; Yoon et al, *World J Gastroenterol*, 2011, (17(35)): 4023-4030), and adenoid cystic carcinoma (Bell et al, *Annals of Diagnostic Pathol-* ogy, 2014, (18): 10-13; Stoeck et al, *Cancer Discov,* 2014, (4): 1154-1167). Inhibition of Notch signaling presents an attractive target to provide therapeutic benefits to cancer patients whose disease was induced by aberrant activation of constitutive Notch signaling pathway. Shih et al. *Cancer Research,* 2007(67)1879-1882.

One of the definitive genes for inner ear hair cell development is the mammalian homolog of the basic helix-loop-helix transcription factor atonal-1 (Atoh1). Expression of Atoh1 in cochlear cells is required for auditory hair cell genesis. Prosensory epithelial cells within the developing organ of Corti that express Atoh1 will differentiate into auditory hair cells (Helms et al, *Development* 2000, (127 (6)); 1185-1196), and Atoh1 is one of the earliest markers of auditory hair cell differentiation. Supporting cells of the organ of Corti maintain the potential to develop hair cell characteristics including cilia formation (Zheng et al, *Nature Neuroscience,* 2000, (3(6)): 580-586; Kawamoto et al, *J Neurosci,* 2003, (23(11)): 4395-4400; Izumikawa et al, *Nat Med,* 2005, (11(3)):271-276; and proper hair cell function (Kawamoto et al, 2003).

Each hair cell in the cochlea is surrounded by non-sensory supporting cells that provide trophic and structural support for the hair cells and ganglion and are essential in maintaining proper ionic concentrations in the organ of Corti through gap junction intercellular communication. There are two types of hair cells: inner and outer hair cells. The cochlear hair cells in mammals including humans, consist of one row of inner hair cells and three rows of outer hair cells. The inner hair cells are the actual sensory receptors, and 95% of the fibers of the auditory nerve that project to the brain arise from this subpopulation. The terminations on the outer hair cells are almost all from efferent axons that arise from cells in the brain and these cells function as acoustical pre-amplifiers. Supporting cells play a key role in auditory hair cell generation after auditory hair cell loss or damage. During development, hair and supporting cells develop from a common progenitor and the appearance of a hair cell signals surrounding cells to develop into supporting cells through contact inhibition mediated by the Notch signaling pathway (Kelley, *Nat Rev Neurosci,* 2006, (11): 837-849).

Based on the ability of supporting cells to transdifferentiate into auditory hair cells, along with their shared developmental pathway, it has been postulated that supporting cells may function as hair cell progenitors (Parker et al, *Audiology and Neurootoloy,* 2004, (9(2)): 72-80). Several studies have demonstrated that bypassing cell cycle inhibition in supporting cells can result in auditory hair cell generation in mammals (Lowenheim et al, *Proc Natl Acad Sci USA,* 1999, (96): 4084-4088; Torchinsky et al, *J Neurocytol,* 1999, (28(10-11)): 913-924; Minoda et al, *Hear Res,* 2007, (232): 44-51). Therefore adult mammalian supporting cells maintain the ability to transdifferentiate into auditory hair cells once they are free to enter the cell cycle.

Drug therapy for restoration of auditory hair cells is a new approach and intratympanic administration to the middle ear fluid, preferably to the round window niche, without actual injection into the cochlea may effectively induce Atoh1 expression at a therapeutic dose and for a suitable length of time to cause auditory hair cell transdifferentiation of supporting cells in the cochlea. Mizutari et al, *Neuron,* 2013, (77(1)): 58-69 showed that middle ear delivery of a gamma secretase inhibitor (LY411575) may be employed to regenerate auditory hair cells lost to acoustic trauma in mice and that this generation of new hair cells from supporting cells resulted in significant, measurable, hearing recovery. This work provided conceptual evidence of a therapeutic effect of Notch pathway signaling inhibition on auditory hair cell generation and restoration of hearing in a mouse model, and provided a mechanistic (supporting cell differentiation to auditory hair cells) explanation for the physiological effect. Dose limiting toxicity was shown during systemic administration of LY411575.

The following in vitro and in vivo studies demonstrate the Notch pathway signaling inhibitory activity and efficacy of Compounds 1 and 2, or a substantially pure diastereomer thereof, against a specific cancer cell line. These assays are generally recognized by those skilled in the art as indicative of human clinical chemotherapeutic activity. Inhibition of Notch intracellular domain cleavage by γ-secretase is believed to be effective against each of Notch 1, Notch 2, Notch 3 and Notch 4 receptors. Assays evidencing Notch pathway signaling inhibitory activity and efficacy may be carried out substantially as follows or by similar assays affording similar data.

Notch1 N1ICD Nuclear Accumulation Cellular Imagine Assay

HEK293ΔE12 cells (HEK293 cells are engineered to stably express mouse Notch1 cDNA coding for amino acid 1703-2183, Np_932740.3, (Full length mouse Notch 1 protein precursor: SEQ ID NO:1) with 23 amino acid signal peptide sequence, MPRLLTPLLCLTLLPALAARGLR (SEQ ID NO:2), at its N-terminus) are plated at 5000 cells/well in 96 well plates, incubated in Dulbecco's Modified. Eagle's Medium (DMEM)-high glucose with 5% fetal bovine serum (FBS) at 37° C., 5% $CO_2$ for 24 hours. Cells are treated with test compound, dosing at 10 points of 1:3 dilutions across the range of 1000 nM to 0.05 nM, and with final dimethyl sulfoxide (DMSO) concentration at 0.2%. After 24 hours treatment, cell plates are processed through following steps sequentially: fix cells with 100 μl/well PREFER™ fixative for 30 minutes at room temperature (RT); permeablize cells with 100 μl/well 0.1% TRITON® X100 in phosphate buffered saline (PBS) for 20 min at RT; wash 3 times with 100 μl/well PBS each; add 50 μl/well rabbit anti-N1ICD (Notch1 Intracellular Domain) antibody, at 1:2000 in PBS with 1% bovine serum albumin and incubate 1.5 hours at 37° C.; wash 3 times with 100 μl/well PBS each; incubate with 50 μl/well goat anti-rabbit IgG (Immunoglobulin G) Alexa 488 at 1:1000 dilution in PBS with 1% bovine serum albumin and incubate 1 hours at 37° C.; wash 3 times with 100 μl/well PBS each and add 100 μl/well 15 μM propidium iodide with 50 μg/ml RNAse for 30 minutes to stain nuclei. Plates are scanned with ACUMEN EXPLORER™ Laser-scanning fluorescence microplate cytometer (TTP LABTECH LTD) to measure total cell nuclear count/well and total nuclear area/well with fluorescence at 655 nm-705 nm (emission of DNA bound propidium iodide) and fluorescence of antibody binding to N1ICD in nuclear region at 505 nm-530 nm. The main assay output is a ratio of total fluorescence of nuclear N1ICD to total nuclear area, the normalized nuclear N1ICD signal. A relative cytotoxicity profiling was collected as % cell number to 0.2% DMSO control cells. The antibody that recognizes cleaved Notch1 or N1ICD is raised to a human peptide corresponding to the amino terminal cleavage site of human Notch1 at Val1744. In untreated control cells, N1ICD generated from Notch1 will translocate and accumulate in nucleus. When cells are treated by a Notch 1 cleavage inhibiting compound, the signal of nuclear N1ICD will decrease. Concentration response and the $IC_{50}$ are determined by curve fitting to a four parameter logistic for the nuclear N1ICD signal, while the % cell number is plotted in the same graph for cytotoxicity profiling. Performing the assay essentially as described above, the average $IC_{50}$ for Compound 1, isomer 2 is 0.37 nM (+/−0.16; n=2) and Compound 2, Isomer 2 is 1.55 nM (+/−1.12; n=2). Neither compound affects cell number up to 1000 nM concentration. These data evidence Compound 1, isomer 2 and Compound 2, Isomer 2 each has affinity for Notch 1 and inhibits the intracellular accumulation of the Notch 1 intracellular domain cell signaling peptide.

In-Vivo Target Inhibition Studies

Animal Studies

To evaluate in vivo effect of Compound 1, Isomer 2 and. Compound 2, Isomer 2 on inhibition of Notch processing pharmacodynamics (PD), animal studies were conducted in non-tumor bearing Balb/C mice (Charles River). A total of 5 mice are used for each group. Mice are fed ad libitum on normal chow. Treatment is initiated with oral administration (gavage) of compound or vehicle (1% Na-CMC in 0.25% Tween-80) in 0.2 mL volume. At designated time points (4 or 8 hours after the dose) following treatment, animals are sacrificed by $CO_2$ asphyxiation and cervical dislocation. Tissues (Lungs) are removed and used for PD response analysis as measured by cleaved N1ICD.

N1ICD Analysis

To evaluate N1ICD levels in lung, approximately 75 mg is cut from the frozen tissue and minced prior to homogenization (actual mass recorded). Frozen tumor samples are transferred to Lysing Matrix-D™ tubes and re-suspended in ice-cold XY lysis buffer (25 mM Tris pH 7.5, 10 µg/ml Trypsin/Chymotrypsin inhibitor, 10 µg/ml Aprotinin, 60 mM Beta-glycerol phosphate, 1% Triton® X-100, 10 mM NaF, 2.5 mM pyrophosphate, 150 mM NaCl, 15 mM ethylene diamine tetra acetic acid (EDTA) pH 8.0, 5 mM ethylene glycol-bis(2-aminoethylether)-N,N,N',N'-tetra acetic acid (EGTA) pH 8.0, 1 mM Na Vanadate, 10 µg/ml Leupeptin, 1 mM dithiothreitol, 1 µM microcystin LR, 10 µg/ml N-p-tosyl-L-phenylalanine chloromethyl ketone (TPCK), 2 mM Nα-p-tosyl-L-arginine methyl ester hydrochloride (TAME), 15 mM 4-nitrophenyl phosphate di(tris) salt (PNPP), 0.1 mM 4-(2-aminoethyl) benzenesulfonyl fluoride hydrochloride (AEBSF), 5 mM benzamidine, 1 µM Okadaic Acid) containing 1× Complete tablet (Roche Complete™ No. 11697 498 001) and 1× Protease Inhibitor cocktail (Sigma-Aldrich P8340) at a mass: volume ratio of 75 mg/ml buffer. Tissues are homogenized in a Fast Prep FP120 homogenizer (Thermo Scientific, Rockford, Ill.) at a speed of 6.0 for 30 seconds at 4° C., followed by 15 minute incubation on ice. This is repeated for a total of 2-3 cycles until homogenization is complete. Lysates are spun in a 4° C. eppendorf centrifuge at 30,000 rpm for 15 minutes to remove debris. 400 µl of supernatant is removed and transferred to a new eppendorf tube and subjected to a freeze/thaw cycle. Samples are re-spun in a 4° C. eppendorf centrifuge at 30,000 rpm for 30 minutes and 120 µl of supernatant is collected for analysis. Total protein concentration is determined using Pierce BCA Protein Assay Kit™ (Thermo Scientific, Rockford, Ill.) using a Thermomax™ plate reader (Molecular Devices, Sunnyvale, Calif.). N1ICD levels are determined using a custom N1ICD ELISA. Analyte is captured with a cleaved Notch1 (Val1744)-specific custom rabbit monoclonal antibody and detected with a C-terminal Notch1 SULFO-TAG™ (Meso Scale Discovery, Gaithersburg, Md.) polyclonal sheep antibody (R&D Systems, Minneapolis, Minn.). Lysates are diluted to 2 µg/µl in ice-cold ELISA tris lysis buffer (R6OTX) (Meso Scale Discovery, Gaithersburg, Md.) containing 1× Complete tablet (Roche Complete™ mini No. 11 836 153 001) and 1× Protease Inhibitor cocktail (Sigma-Aldrich P8340), and 25 µl is added to the ELISA plate. Incubation of 50 µg protein lysate is done at RT for one hour each to capture analyte and with detection antibody. Plates are read on a Sector Imager 6000™ (Meso Scale Discovery, Gaithersburg, Md.). Background subtracted N1ICD is normalized to total protein and presented as % inhibition relative to the vehicle-treated group. N1ICD % inhibition and statistical significance (p value) as measured by Dunett's method in tumors harvested 4 hours after last dose for Compound 1, Isomer 2 or Compound 2, Isomer 2 is analyzed essentially as described above and summarized in Table 1.

TABLE 1

| Compound | Dose (mg/kg) | Time (hours) following treatment | % N1ICD inhibition (Ave ± SD; n = 1) | p Value |
| --- | --- | --- | --- | --- |
| 1, Isomer 2 | 10 | 4 | 70 ± 12 | <0.0001 |
| 1, Isomer 2 | 10 | 8 | 65 ± 11 | <0.0001 |
| 1, Isomer 2 | 100 | 8 | 92 ± 3 | <0.0001 |
| 1, Isomer 2 | 30 | 8 | 87 ± 3 | <0.0001 |
| 1, Isomer 2 | 10 | 8 | 52 ± 31 | 0.0054 |
| 1, Isomer 2 | 3 | 8 | 11 ± 13 | Not Significant |
| 1, Isomer 2 | 1 | 8 | 6 ± 15 | Not Significant |
| 1, Isomer 2 | 0.3 | 8 | −7 ± 26 | Not Significant |
| 2, Isomer 2 | 10 | 4 | 65 ± 11 | <0.0001 |
| 2, Isomer 2 | 10 | 8 | 15 ± 14 | Not Significant |

The data in Table 1 evidences the inhibition of N1ICD cleavage by Compound 1, Isomer 2 and Compound 2, Isomer 2 in mouse lung tissue. The data in Table 1 further provides an in vivo correlation to the functional activity data described above.

Induction of mAtoh1 Expression in Otic Spheres

Generally, organ of Corti cell isolation is carried out on Day 0, largely by the method in Oshima et al., *Methods Mol Biol.*, 2009; 493: 141-162. Cell culture and propagation are carried out for 3-4 days. Cell plating and test compound treatment takes place on Day 3 or 4. Attachment and differentiation is allowed to take place over the next 7 days. On Days 10 or 11, cell lysis and RNA isolation is carried out. TaqMan qRT-PCR is carried out on Day 12 and the results analyzed on Days 13-15 for Atoh1 and Tbp1 expression.

Isolation of Cells

Surrounding tissue from the petrous portion of the temporal bone are removed from 1 to 4 day-old postnatal mice (transgenic strain: mAtoh1-driven nGFP; Lumpkin E A, et al., *Gene Expr Patterns,* 2003; (36): 389-95 of both sexes. The conch shaped cochlea is separated from the vestibular system using forceps. At this stage of development, the bony labyrinth is not completely calcified and is easily dissected using forceps. Carefully open the bony labyrinth of the cochlea and remove the spiral ligament and attached organ of Corti coiled together along the spiral of the modiolus by unwinding apically from the modiolus. Starting at the base, separate the spiral ligament from the organ of Corti using fine forceps.

Transfer the dissected organ of Corti (OC) into individual 1.5 ml tubes filled with 850 ice cold HBSS. Transfer up to 12 OC tissues into the same tube, Quick-spin down OC tissues and remove the HBSS. Disassociate the cells by adding 100 µl pre-warmed TrypLE™ Select (Life Technologies) and incubate at 37° C. for 13 min. Quick spin down dissociated OC tissues. Remove TrypLE™ Select. Add 100 µl of Medium A (DMEM/F12, N2 supplement (LifeTechnologies), B27 supplement (LifeTechnologies), ampicillin (50 µg/ml) and Fungizone (LifeTechnologies), EGF (20 ng/ml), bFGF (10 ng/ml), IGF-1 50 ng/ml), and heparan sulfate (50 ng/ml)). The dissected and digested tissue is then triturated with a P200 pipette tip. Remove any cell aggregates and debris; transfer the cell suspension and wash through a pre-wetted 70 µm cell strainer to pool the cell suspension in a single fresh culture tube. Rinse dissociation tubes and the cell strainer with sufficient Medium A and pool with the cell suspension. Count cell density with hemocytometer or Countess® (Life Technologies). Add fresh Medium A to cell suspension to achieve a final plating density of 1.0E5 cell/ml and plate into ultra-low attachment cultureware, T-75 (Greiner).

Culturing in Suspension to Propagate OC Spheres

The dissociated, single cells are cultured in an ultra-low attachment cultureware, (Greiner) in Medium A for 3 to 4 days in a 5% $CO_2$ humidified incubator at 37° C. to obtain clonally grown spheres, termed first generation spheres, from the floating cells. If cells stick to the non-adherent dishes during the culture period they can be dislodged by gentle mixing.

Attachment Culture and Treatment

After culturing the spheres for 3-4 days, visually count the spheres by microscope to standardize the seeding density of otic spheres per ml for this step. Collect the cells by centrifugation and re-suspend spheres in Basic Medium at a concentration of approximately 2000 spheres per ml. Seed the spheres in a volume of 150 µl per well of a cell culture-treated 96 well plate to obtain approximately 300 spheres per well. Treat the spheres with experimental agents in quadruplicate at a final volume of 200 µl in Basic Medium (DMEM/F12, N2 supplement (LifeTechnologies) B27 supplement (LifeTechnologies), ampicillin (50 µg/ml) and Fungizone (LifeTechnologies). Culture the treated spheres for 7 days in a humidified temperature controlled incubator at 5% $CO_2$, 37° C. Remove medium and proceed with RNA extraction.

RNA Extraction

Add buffer RLT plus (Qiagen) supplemented with 1% Beta-mercaptoethanol, 175 µl per well. Add 2.5 µl of 4 ng/µl of RNA carrier (RNeasy® Plus Micro Kit; Qiagen) diluted in Buffer RLT Plus into each well before RNA extraction. Total RNA is extracted using the RNeasy® Plus Micro Kit (Qiagen) according to the manufacturer's instructions.

cDNA Synthesis cDNA synthesis is carried out using the SuperScript® III First-Strand Synthesis System (LifeTechnologies, catalogue 18080-051) following the manufacturer's protocol using random hexamers for cDNA synthesis. Dilute cDNA 50% by adding 21 µl of ultra-pure nuclease-free water. 5 µl of diluted cDNA is used for qPCR.

qPCR

To quantify the expression of hair cell markers from the treated sphere cultures, qPCR with probes to detect a gene of interest mAtoh1 and an endogenous control gene is carried out in a single, two-color multiplex reaction. TaqMan Gene Expression Master Mix (LifeTechnologies, 4369016) and a probe of interest (Atoh1; Mm00476035_s1 and an endogenous control probe (Tbp1; Mm00446971_m1, LifeTechnologies) is used according to the manufacturer's instructions. Conditions are kept constant for each probe. Relative gene expression between treatment groups is analyzed using the $\Delta\Delta C_T$ method and replicate measurements are averaged. Experiments are carried out in triplicate, at a minimum, and reported as a grand mean.

TABLE 2

| Compound | RQ at 10 nM | RQ at 100 nM | RQ at 1 µM |
|---|---|---|---|
| 1, Isomer 2 | 1.43 ± 0.17* | 1.76 ± 0.17* | 1.64 ± 0.13* |
| 2, Isomer 2 | 1.14 ± 0.07 | 1.21 ± 0.13 | 1.57 ± 0.11* |

The data in Table 2 shows relative quantitation values (RQ) of Atoh1 expression, a marker of hair cell generation, in otic spheres treated with each of Compound 1, Isomer 2 and Compound 2, Isomer 2 at three concentrations (10 nM, 100 nM and 1 µM). Data (±standard error of the mean, SEM) represent the gene expression fold-induction relative to negative control (DMSO carrier)-treated samples. (*, significant difference from negative control, $p<0.05$).

Induction of hAtOh1 Expression in Human Tumor Cell Lines

To evaluate potency of Compounds 1, Isomer 2 and 2, Isomer 2 in their ability to induce hAtoh1 expression, a human tumor cell line is utilized. Endogenous Notch signaling regulation for this cell line is similar to that in the inner ear. Generally, this assay is carried out following principles in Kazanjian et al., *Gastroenterology*, 2010, 139 (3): 918-928 and Supplementary Materials and Methods.

Generally, standard cell culture techniques are used. Low passage human colorectal adenocarcinoma cell line LS174T (ATCC CL-188) maintained in Growth Medium (MEM 10% FBS) is plated 10,000 cells in 100 µl Assay Medium (MEM 1% FBS) per well into 96-well tissue culture treated plates.

The following day, half-log serial dilutions of 10 mM stock test compounds (diluted in 100% DMSO) were carried out to obtain eleven decreasing doses of drug compound. Final concentrations are to span 10 µM to 0.127 nM. A 3.16-fold serial dilution is used, with DMSO concentrations in each well of 100%. A further 1:10 dilution of the initial DMSO dilution is carried out into Assay Medium. Another dilution of 1:100 again into Assay Medium is carried out.

100 µl of the test compound dilutions are added to each well containing cells and Growth Media and grown for 72 hours at 37° C. in 5% $CO_2$.

Cells are collected from the plates on day 4, and the RNA extracted and purified using RNeasy® Plus 96 RNA (Qiagen) following the manufacturer's protocol.

cDNA synthesis is carried out using the SuperScript® III First-Strand Synthesis System (LifeTechnologies, 18080-051) following the manufacturer's protocol using random hexamers for cDNA synthesis. The cDNA is diluted 50% by adding 21 µl of ultra-pure nuclease-free water. 5 µl of the diluted cDNA is used for qPCR.

qPCR

To quantify the expression of hair cell markers from the treated sphere cultures, qPCR probes to detect hAtoh1 or TBP expression in a single two-color multiplex reaction is carried out. To measure relative gene expression for each sample, TaqMan Gene Expression Master Mix (LifeTechnologies, 4369016) and a probe of interest (human Atoh1; LifeTechnologies Assay Id Hs00944192_s1) plus an endogenous control (human TBP; LifeTechnologies Assay Id Hs00427620_m1) is used according to the manufacturer's instructions. Conditions are kept constant for each probe. Relative gene expression between treatment groups is analyzed using the $\Delta\Delta C_T$ method and replicate measurements are averaged.

Four separate assays are carried out to obtain $IC_{50}$ values for each test compound. The $IC_{50}$ value is determined by fitting concentration response data to "log(antagonist) vs. response (three parameter)" model using GraphPad Prism® software for 12 doses across a concentration range of 4.0E-11 to 1.0E-6 M with 108 total points analyzed for each compound. The $IC_{50}$ value for Compounds 1, Isomer 2 and 2, Isomer 2 are shown in Table 3.

TABLE 3

| Compound | $IC_{50}$ nM |
| --- | --- |
| 1, Isomer 2 | 16.64 |
| 2, Isomer 2 | 54.34 |

The data in Table 3 shows $IC_{50}$ values of Compound 1, Isomer 2 and Compound 2, Isomer 2 as calculated by the relative expression of hAtoh1, a marker of auditory hair cell generation in this assay.

Response to Compounds in an Organ of Corti Explant Assay

Generally, organ of Corti organotypic explant culture is carried out on Day 0 according to the method described in Parker et al., *Journal of Visualized Experiments*, 2010, (36), e1685. Explant culture is carried out for 4-7 days at which point the culture is either prepared for cellular lysis for qRT-PCR, or tissue fixation for immunohistochemistry.

Isolation and Culture of Organ of Corti Explants

The bulla and surrounding tissue from the petrous portion of the temporal bone are removed from 1 to 4 day-old postnatal mice (transgenic strain: Atoh1-driven nGFP; Lumpkin E A, et al., *Gene Expr Patterns*, 2003, (36):389-95) of both sexes. Organs of Corti are dissected in Hanks solution, the spiral ligament is removed and the explants are placed on cover slips coated with poly-L-ornithine (0.01%, Sigma) and laminin (50 mg/ml, Becton Dickinson) to obtain a preparation with a flat cochlear surface. Each cochlear explant is then placed in a single well of a 24 well plate (Falcon) and cultured in DMEM (Invitrogen) with 5% fetal bovine serum, 5% horse serum, and penicillin-streptomycin (LifeTechnologies). Experimental compounds are added with medium on Day 0 and replaced every 2-3 days. All cultures are maintained in a 5% $CO_2$ humidified incubator at 37° C.

Gene Expression Analysis by qRT-PCR

RNA Extraction is carried out by lysing the explant tissue with 350 µl RLT Plus buffer (Qiagen) per well, and total RNA is purified by RNeasy® Plus Mini Kit (Qiagen). cDNA synthesis is carried out with the SuperScript® III First-Strand Synthesis System (LifeTechnologies) using random hexamers. To quantify the induction of hair cell marker expression, qPCR is performed with TaqMan Gene Expression Master Mix (LifeTechnologies, 4369016) and probes to detect genes of interest (e.g. hAtoh1; Assay ID Mm00476035_s1, Pou4f3; Assay ID Mm04213795_s1 and Myo7a; Assay ID Mm01274015_m1, LifeTechnologies) and an endogenous control gene, Tbp (Assay ID Mm00446971_m1, LifeTechnologies). Relative gene expression between treatment groups is analyzed using the $\Delta\Delta C_T$ method and replicate measurements are averaged. Experiments are carried out in triplicate, at a minimum, and reported as a grand mean.

TABLE 4

| Compound | Atoh1 | Pou4f3 | Myo7a |
| --- | --- | --- | --- |
| 1, Isomer 2 | 3.72 ± 0.54 | 2.04 ± 0.35 | 1.73 ± 0.33 |
| 2, Isomer 2 | 3.10 ± 0.69 | 1.65 ± 0.25 | 1.49 ± 0.22 |

The data in Table 4 shows relative quantitation values (RQ) of expression of the hair cell generation markers; Atoh1, Pou4f3, and Myo7a, in organ of Corti explants treated with Compound 1, Isomer 2 and Compound 2, Isomer 2 at 1 µM. Data (±SEM) represent the fold-induction in gene expression relative to negative control-treated samples.

Immuno-Staining of New Atoh1-Expressing Hair Cells

Following the explant culture, tissues are fixed in the 24 well plate with 200 µl Cytofix/Cytoperm (BD) for 30 min, rinsed with PBS containing TritonX100 (PBST), and stained with 200 µl of primary antibody solution, consisting of 4% normal donkey serum in PBST with goat anti-GFP (1:2500; AbCAM, ab5450) and rabbit anti-myosinVIIa (1:1000; Proteus Bioscience #25-6790) for 1 hour. The tissues are then thoroughly washed with PBST and stained with a secondary antibody solution, consisting of Alexa Fluor 488 donkey anti-goat IgG (1:1000; InvitrogenA-11055) and Alexa Fluor 568 donkey anti-rabbit IgG (1:1000; Invitrogen, A10042) for 1 hour. They are then thoroughly washed with PBST and mounted on microscope slides. Individual hair cells are identified by expression of the Atoh1-surrogate marker GFP (Green) and myosin VIIa (red), imaged, and then counted within a 100 length at the mid-apex region in order to examine the formation of nascent hair cells in experimental, compound-treated samples in contrast to hair cell numbers in untreated or negative control (biological inactive compound)-treated samples. Blinded cell counts are measured in five separate experiments.

TABLE 5

| Compound | Number of Outer Hair Cells (per 100 µM) | Percent Increase |
| --- | --- | --- |
| 1, Isomer 2 | 50.4 ± 4.9 | 14.15 ± 1.9% |
| 2, Isomer 2 | 55.8 ± 3.1 | 17.26 ± 1.2% |

The data in Table 5 shows outer hair cell numbers in organ of Corti explants cultured for four days in the presence of Compound 1, Isomer 2 (n=13) or Compound 2. Isomer 2 (n=15) at 1 µM, and immunostained for GFP (a surrogate Atoh1 marker) and myosin VIIa. Percent increase in hair cells are relative to negative control-treated samples (n=18).

Gene Expression Analysis after Ototoxic Damage

A variation of the organ of Corti organotypic explant culture is used to model hair cell regeneration in response to subsequent compound treatment after ototoxic damage. This damage model is carried out according to the method described in Korrapati et al., *PLOSOne,* 2013, 8(8), e73276 where a 95% reduction in mid-apical hair cells was reported. On Day 0, to damage and selectively kill hair cells within the organ of Corti explant, aminoglycoside treatment (gentamicin (100 µM)) is added for 18-24 hours. On Day 1, gentamicin is removed and treatment with Compound 1, Isomer 2 and Compound 2, Isomer 2 at 5 µM began. Explant culture continues for 4 days total at which point the culture is prepared for the qRT-PCR protocol described above. Visible confirmation of gentamicin-induced damage is easily observed between cultures treated with negative control compounds. However, quantitative measurement for the response to Compound 1, Isomer 2 and Compound 2, Isomer 2 treatment following ototoxic damage obtained by qRT-PCR measured increases in gene expression for prosensory hair cell markers Atoh1 and Pou4f3 and the hair cell marker Myo7A.

TABLE 6

| Compound (5 µM) | % Induction Over Control-treated Damaged Organ of Corti (Mean ± SEM; p Value) n = 11 | | |
|---|---|---|---|
| | Atoh1 | Pou4f3 | Myo7A |
| 1, Isomer 2 | 242 ± 16; <0.0005* | 114 ± 25; <0.05* | 102 ± 18; 0.0522 |
| 2, Isomer 2 | 169 ± 24; <0.05* | 28 ± 11; 0.0633 | 52 ± 15; not signif. |

The data in Table 6 shows relative increases in gene expression by qRT-PCR of the hair cell generation markers Atoh1, Pou4f3, and Myo7a, in organ of Corti explants treated with Compound 1, Isomer 2 and Compound 2, Isomer 2 at 5 µM after gentamicin (100 µM) damage. Data represent the percent increase in gene expression relative to negative control-treated samples with the gentamicin-induced hair cell damage. (*, significant difference from negative control, p<0.05)

Hair Cell Marker Induction in Whole Otic Capsule Culture

The otic capsule (otic capsule explant), comprised of the cochlear bony labrinth and vestibular systems, is dissected from 1 to 4 day-old postnatal mice (transgenic strain: Atoh 1-driven nGFP; Lumpkin E A, et al., *Gene Expr. Patterns,* 2003, 3(4): 389-95) of both sexes generally according to the method described in Parker et al., *Journal of Visualized Experiments,* 2010, (36), e1685. The entire otic capsule is isolated from the parietal bone and maintained ex-vivo in a roller tube culture system for up to 3 days in medium containing DMEM, high glucose, 5% FBS, 5% horse serum, 1 µg/ml ampicillin.

The otic capsule explant is used to evaluate test compound, in various delivery vehicles, penetrance into the inner ear. Tests are carried out with compositions of Compound 1, Isomer 2, (7.2 mM) in various delivery vehicles. Small volumes (100-200 nl) are directly applied to the round window niche of the cochlea. The cochlea is dissected, treated, incubated for 1-2 hrs, then entered into the roller culture. After 48 hrs. the otic capsule explant is opened to remove the organ of Corti from the bony labyrinth of the cochlea and assayed by RT-PCR.

The composition is allowed to remain for 1-2 hours then washed away with culture medium. The otic capsule explant is then cultured for 48 hours in untreated medium. The cochlea is broken open and the entire organ of Corti is then dissected out and prepared for quantitative RT-PCR to measure Atoh1 hair cell marker expression levels (as described in organ of Corti explant assay, above). Table 7 shows Atoh1 induction in the specified delivery vehicle. Up-regulation of Atoh1 by Compound 1, Isomer 2, in all tested compositions (2-3 fold, n of 12-17) is measured in comparison to vehicle-only control-treated otic capsule explants after 48 hours in culture.

TABLE 7

| Atoh1 Gene Expression (RT-PCR) | | | | |
|---|---|---|---|---|
| | 45-70% PEG (Polyethylene glycol 400) | 10% Poloxamer (Pluronic ® F108) | 20% Poloxamer (Pluronic ® F108) | 1-2% Hyaluronic Acid |
| Liquid state | Viscous liquid | Viscous liquid | Gel | Gel |
| Test compound solubility | Clear solution | Suspension | Suspension | Suspension |
| Mean Fold-Induction | 2.933 | 2.398 | 2.612 | 2.459 |
| SEM | 0.3193 | 0.2653 | 0.4441 | 0.2567 |
| P value | <0.0001 | 0.0002 | 0.0019 | 0.0001 |

In Vivo Perilymph Test Compound Uptake into Inner Ear

Female albino Hartley guinea pigs (Charles River, France) are anesthetized with a mixture of ketamine/xylazine prior to 70 µl of Compound 1, Isomer 2, in compositions as described above for Whole otic capsule culture assay are injected by transtympanic route to completely fill the middle ear. Perilymph (inner ear fluid) samples are extracted at 0.5, 1, 6, 24 and 48 hours post-injection and assayed by LCMS (n of 5) for concentration of test compound. Table 8 shows test compound is taken up into the inner ear following transtympanic administration to the middle ear with these delivery vehicles.

TABLE 8

| IN VIVO Perilymph Levels | | | | |
|---|---|---|---|---|
| | 70% PEG (Polyethylene glycol 400) | 10% Poloxamer (Pluronic ® F108) | 20% Poloxamer (Pluronic ® F108) | 1% Hyaluronic Acid |
| Cmax (µM) ± SEM | 327.1 ± 93 | 753.0 ± 306 | 1926.2 ± 493 | 187.3 ± 113 |
| Time Cmax | 1 hr | 30 min | 30 min | 1 hr |
| % Applied Test Compound in perilymph | 1.04 | 2.39 | 6.11 | 0.59 |
| R squared | 0.5262 | 0.7640 | 0.5600 | 0.4229 |
| AUC (µmol · hr · L$^{-1}$) | 1451 | 7002 | 8634 | 2711 |

Amino Acid Sequences

SEQ ID NO: 1 (Mouse Notch 1 protein precursor; full length)
MPRLLTPLLCLTLLPALAARGLRCSQPSGTCLNGGRCEVANGTEACVCSG
AFVGQRCQDSNPCLSTPCKNAGTCHVVDHGGTVDYACSCPLGFSGPLCLT
PLDNACLANPCRNGGTCDLLTLTEYKCRCPPGWSGKSCQQADPCASNPCA
NGGQCLPFESSYICRCPPGFHGPTCRQDVNECSQNPGLCRHGGTCHNEIG
SYRCACRATHTGPHCELPYVPCSPSPCQNGGTCRPTGDTTHECACLPGFA
GQNCEENVDDCPGNNCKNGGACVDGVNTYNCRCPPEWTGQYCTEDVDECQ
LMPNACQNGGTCHNTHGGYNCVCNGWTGEDCSENIDDCASAACFQGATCH
DRVASFYCECPHGRTGLLCHLNDACISNPCNEGSNCDTNPVNGKAICTCP
SGYTGPACSQDVDECALGANPCEHAGKCLNTLGSFECQCLQGYTGPRCEI
DVNECISNPCQNDATCLDQIEFQCICMPGYEGVYCEINTDECASSPCLHN
GHCMDKINEFQCQCPKGFNGHLCQYDVDECASTPCKNGAKCLDGPNTYTC
VCTEGYTGTHCEVDIDECDPDPCHYGSCKDGVATFTCLCQPGYTGHHCET
NINECHSQPCRHGGTCQDRDNSYLCLCLKGTTGPNCEINLDDCASNPCDS
GTCLDKIDGYECACEPGYTGSMCNVNIDECAGSPCHNGGTCEDGIAGFTC
RCPEGYHDPTCLSEVNECSNPCIHGACRDGLNGYKCDCAPGWSGTNCDI
NNNECESNPCVNGGTCKDMTSGYVCTCREGFSGPNCQTNINECASNPCLN
QGTCIDDVAGYKCNCPLPYTGATCEVVLAPCATSPCKNSGVCKESEDYES
FSCVCPTGWQGQTCEVDINECVKSPCRHGASCQNTNGSYRCLCQAGYTGR
NCESDIDDCRPNPCHNGGSCTDGINTAFCDCLPGFQGAFCEEDINECASN
PCQNGANCTDCVDSYTCTCPVGFNGIHCENNTPDCTESSCFNGGTCVDGI
NSFTCLCPPGFTGSYCQYDVNECDSRPCLHGGTCQDSYGTYKCTCPQGYT
GLNCQNLVRWCDSAPCKNGGRCWQTNTQYHCECRSGWTGVNCDVLSVSCE
VAAQKRGIDVTLLCQHGGLCVDEGDKHYCHCQAGYTGSYCEDEVDECSPN
PCQNGATCTDYLGGFSCKCVAGYHGSNCSEEINECLSQPCQNGGTCIDLT
NSYKCSCPRGTQGVHCEINVDDCHPPLDPASRSPKCFNNGTCVDQVGGYT
CTCPPGFVGERCEGDVNECLSNPCDPRGTQNCVQRVNDFHCECRAGHTGR
RCESVINGCRGKPCKNGGVCAVASNTARGFICRCPAGFEGATCENDARTC
GSLRCLNGGTCISGPRSPTCLCLGSFTGPECQFPASSPCVGSNPCYNQGT
CEPTSENPFYRCLCPAKFNGLLCHILDYSFTGGAGRDIPPPQIEEACELP
ECQVDAGNKVCNLQCNNHACGWDGGDCSLNFNDPWKNCTQSLQCWKYFSD
GHCDSQCNSAGCLFDGFDCQLTEGQCNPLYDQYCKDHFSDGHCDQGCNSA
ECEWDGLDCAEHVPERLAAGTLVLVVLLPPDQLRNNSFHFLRELSHVLHT
NVVFKRDAQGQQMIFPYYGHEEELRKHPIKRSTVGWATSSLLPGTSGGRQ
RRELDPMDIRGSIVYLEIDNRQCVQSSSQCFQSATDVAAFLGALASLGSL
NIPYKIEAVKSEPVEPPLPSQLHLMYVAAAAFVLLFFVGCGVLLSRKRRR
QHGQLWFPEGFKVSEASKKKRREPLGEDSVGLKPLKNASDGALMDDNQNE
WGDEDLETKKFRFEEPVVLPDLSDQTDHRQWTQQHLDAADLRMSAMAPTP
PQGEVDADCMDVNVRGPDGFTPLMIASCSGGGLETGNSEEEEDAPAVISD
FIYQGASLHNQTDRTGETALHLAARYSRSDAAKRLLEASADANIQDNMGR
TPLHAAVSADAQGVFQILLRNRATDLDARMHDGTTPLILAARLAVEGMLE
DLINSHADVNAVDDLGKSALHWAAAVNNVDAAVVLLKNGANKDMQNNKEE
TPLFLAAREGSYETAKVLLDHFANRDITDHMDRLPRDIAQERMHHDIVRL
LDEYNLVRSPQLHGTALGGTPTLSPTLCSPNGYLGNLKSATQGKKARKPS
TKGLACGSKEAKDLKARRKKSQDGKGCLLDSSSMLSPVDSLESPHGYLSD
VASPPLLPSPFQQSPSMPLSHLPGMPDTHLGISLLNVAAKPEMAALAGGS
RLAFEPPPPRLSHLPVASSASTVLSTNGTGAMNFTVGAPASLNGQCEWLP
RLQNGMVPSQYNPLRPGVTPGTLSTQAAGLQHSMMGPLHSSLSTNTLSPI
IYQGLPNTRLATQPHLVQTQQVQPQNLQLQPQNLQPPSQPHLSVSSAANG
HLGRSFLSGEPSQADVQPLGPSSLPVHTILPQESQALPTSLPSSMVPPMT
TTQFLTPPSQHSYSSSPVDNTPSHQLQVPEHPFLTPSPESPDQWSSSSPH
SNISDWSEGISSPPTTMPSQITHIPEAFK SEQ ID NO: 2 (signal peptide)
MPRLLTPLLCLTLLPALAARGLR

We claim:

1. A compound of the structure:

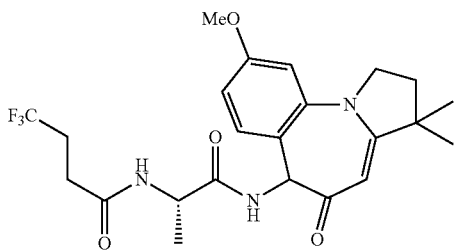 [SMILES: COc1ccc2c(c1)N1CCC(C)(C)C1=CC(=O)C2NC(=O)[C@H](C)NC(=O)CCC(F)(F)F]

or a pharmaceutically acceptable salt thereof.

2. A compound of the structure:

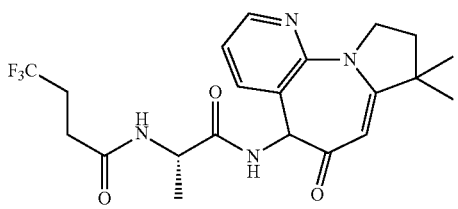 [SMILES: C[C@H](NC(=O)CCC(F)(F)F)C(=O)NC1C(=O)C=C2N(CCC2(C)C)c2ncccc21]

or a pharmaceutically acceptable salt thereof.

3. A pharmaceutical composition comprising the compound of claim 1, or a pharmaceutically acceptable salt thereof, and a pharmaceutically acceptable carrier.

4. A method of treating colorectal cancer in a patient comprising administering to a patient in need thereof a therapeutically effective amount of the compound of claim 1, or a pharmaceutically acceptable salt thereof.

5. A method of treating sensorineural hearing loss caused by auditory hair cell loss in a patient in need thereof, comprising administering to said patient a therapeutically effective amount of the compound of claim 1, or a pharmaceutically acceptable salt thereof.

6. A method of inducing auditory hair cell generation in a patient in need thereof, comprising administering to said patient a therapeutically effective amount of the compound of claim 1, or a pharmaceutically acceptable salt thereof.

7. A pharmaceutical composition comprising the compound of claim 2, or a pharmaceutically acceptable salt thereof, and a pharmaceutically acceptable carrier.

8. A method of treating colorectal cancer in a patient comprising administering to a patient in need thereof a therapeutically effective amount of the compound of claim 2, or a pharmaceutically acceptable salt thereof.

9. A method of treating sensorineural hearing loss caused by auditory hair cell loss in a patient in need thereof, comprising administering to said patient a therapeutically effective amount of the compound of claim 2, or a pharmaceutically acceptable salt thereof.

10. A method of inducing auditory hair cell generation in a patient in need thereof, comprising administering to said patient a therapeutically effective amount of the compound of claim 2, or a pharmaceutically acceptable salt thereof.

11. A substantially pure diastereomer of the compound of claim 1, or a pharmaceutically acceptable salt thereof.

12. A substantially pure diastereomer of the compound of claim 2, or a pharmaceutically acceptable salt thereof.

* * * * *

SEQUENCE LISTING

```
<160> NUMBER OF SEQ ID NOS: 2

<210> SEQ ID NO 1
<211> LENGTH: 2531
<212> TYPE: PRT
<213> ORGANISM: Mus musculus

<400> SEQUENCE: 1

Met Pro Arg Leu Leu Thr Pro Leu Leu Cys Leu Thr Leu Leu Pro Ala
1               5                   10                  15

Leu Ala Ala Arg Gly Leu Arg Cys Ser Gln Pro Ser Gly Thr Cys Leu
            20                  25                  30

Asn Gly Gly Arg Cys Glu Val Ala Asn Gly Thr Glu Ala Cys Val Cys
        35                  40                  45
```

```
Ser Gly Ala Phe Val Gly Gln Arg Cys Gln Asp Ser Asn Pro Cys Leu
 50                  55                  60
Ser Thr Pro Cys Lys Asn Ala Gly Thr Cys His Val Val Asp His Gly
 65                  70                  75                  80
Gly Thr Val Asp Tyr Ala Cys Ser Cys Pro Leu Gly Phe Ser Gly Pro
                 85                  90                  95
Leu Cys Leu Thr Pro Leu Asp Asn Ala Cys Leu Ala Asn Pro Cys Arg
            100                 105                 110
Asn Gly Gly Thr Cys Asp Leu Leu Thr Leu Thr Glu Tyr Lys Cys Arg
        115                 120                 125
Cys Pro Pro Gly Trp Ser Gly Lys Ser Cys Gln Gln Ala Asp Pro Cys
130                 135                 140
Ala Ser Asn Pro Cys Ala Asn Gly Gly Gln Cys Leu Pro Phe Glu Ser
145                 150                 155                 160
Ser Tyr Ile Cys Arg Cys Pro Pro Gly Phe His Gly Pro Thr Cys Arg
                165                 170                 175
Gln Asp Val Asn Glu Cys Ser Gln Asn Pro Gly Leu Cys Arg His Gly
            180                 185                 190
Gly Thr Cys His Asn Glu Ile Gly Ser Tyr Arg Cys Ala Cys Arg Ala
        195                 200                 205
Thr His Thr Gly Pro His Cys Glu Leu Pro Tyr Val Pro Cys Ser Pro
210                 215                 220
Ser Pro Cys Gln Asn Gly Gly Thr Cys Arg Pro Thr Gly Asp Thr Thr
225                 230                 235                 240
His Glu Cys Ala Cys Leu Pro Gly Phe Ala Gly Gln Asn Cys Glu Glu
                245                 250                 255
Asn Val Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe Gln Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ala Leu Gly Ala Asn Pro Cys Glu His Ala Gly Lys Cys Leu Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Ile Ser Asn Pro Cys Gln Asn Asp
450                 455                 460
```

-continued

```
Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
                485                 490                 495

Ser Pro Cys Leu His Asn Gly His Cys Met Asp Lys Ile Asn Glu Phe
            500                 505                 510

Gln Cys Gln Cys Pro Lys Gly Phe Asn Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
        595                 600                 605

Ser Gln Pro Cys Arg His Gly Gly Thr Cys Gln Asp Arg Asp Asn Ser
610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
        675                 680                 685

Asn Gly Gly Thr Cys Glu Asp Gly Ile Ala Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
            820                 825                 830

Cys Ala Thr Ser Pro Cys Lys Asn Ser Gly Val Cys Lys Glu Ser Glu
        835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Lys Ser Pro Cys Arg His
865                 870                 875                 880
```

-continued

Gly Ala Ser Cys Gln Asn Thr Asn Gly Ser Tyr Arg Cys Leu Cys Gln
            885                 890                 895

Ala Gly Tyr Thr Gly Arg Asn Cys Glu Ser Asp Ile Asp Cys Arg
        900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Gln Gly Ala Phe Cys Glu Glu
    930                 935                 940

Asp Ile Asn Glu Cys Ala Ser Asn Pro Cys Gln Asn Gly Ala Asn Cys
945                 950                 955                 960

Thr Asp Cys Val Asp Ser Tyr Thr Cys Thr Cys Pro Val Gly Phe Asn
            965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
            995                 1000                1005

Cys Pro Pro Gly Phe Thr Gly Ser Tyr Cys Gln Tyr Asp Val Asn
    1010                1015                1020

Glu Cys Asp Ser Arg Pro Cys Leu His Gly Gly Thr Cys Gln Asp
    1025                1030                1035

Ser Tyr Gly Thr Tyr Lys Cys Thr Cys Pro Gln Gly Tyr Thr Gly
    1040                1045                1050

Leu Asn Cys Gln Asn Leu Val Arg Trp Cys Asp Ser Ala Pro Cys
    1055                1060                1065

Lys Asn Gly Gly Arg Cys Trp Gln Thr Asn Thr Gln Tyr His Cys
    1070                1075                1080

Glu Cys Arg Ser Gly Trp Thr Gly Val Asn Cys Asp Val Leu Ser
    1085                1090                1095

Val Ser Cys Glu Val Ala Ala Gln Lys Arg Gly Ile Asp Val Thr
    1100                1105                1110

Leu Leu Cys Gln His Gly Gly Leu Cys Val Asp Glu Gly Asp Lys
    1115                1120                1125

His Tyr Cys His Cys Gln Ala Gly Tyr Thr Gly Ser Tyr Cys Glu
    1130                1135                1140

Asp Glu Val Asp Glu Cys Ser Pro Asn Pro Cys Gln Asn Gly Ala
    1145                1150                1155

Thr Cys Thr Asp Tyr Leu Gly Gly Phe Ser Cys Lys Cys Val Ala
    1160                1165                1170

Gly Tyr His Gly Ser Asn Cys Ser Glu Glu Ile Asn Glu Cys Leu
    1175                1180                1185

Ser Gln Pro Cys Gln Asn Gly Gly Thr Cys Ile Asp Leu Thr Asn
    1190                1195                1200

Ser Tyr Lys Cys Ser Cys Pro Arg Gly Thr Gln Gly Val His Cys
    1205                1210                1215

Glu Ile Asn Val Asp Asp Cys His Pro Pro Leu Asp Pro Ala Ser
    1220                1225                1230

Arg Ser Pro Lys Cys Phe Asn Asn Gly Thr Cys Val Asp Gln Val
    1235                1240                1245

Gly Gly Tyr Thr Cys Thr Cys Pro Pro Gly Phe Val Gly Glu Arg
    1250                1255                1260

Cys Glu Gly Asp Val Asn Glu Cys Leu Ser Asn Pro Cys Asp Pro
    1265                1270                1275

-continued

```
Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Arg Gly Lys Pro Cys Lys Asn Gly Val Cys Ala
    1310                1315                1320

Val Ala Ser Asn Thr Ala Arg Gly Phe Ile Cys Arg Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Ser Phe Thr Gly Pro Glu Cys
    1370                1375                1380

Gln Phe Pro Ala Ser Ser Pro Cys Val Gly Ser Asn Pro Cys Tyr
    1385                1390                1395

Asn Gln Gly Thr Cys Glu Pro Thr Ser Glu Asn Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Thr Gly Gly Ala Gly Arg Asp Ile Pro Pro Pro
    1430                1435                1440

Gln Ile Glu Glu Ala Cys Glu Leu Pro Glu Cys Gln Val Asp Ala
    1445                1450                1455

Gly Asn Lys Val Cys Asn Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Leu Thr Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Leu Val Val
    1565                1570                1575

Leu Leu Pro Pro Asp Gln Leu Arg Asn Asn Ser Phe His Phe Leu
    1580                1585                1590

Arg Glu Leu Ser His Val Leu His Thr Asn Val Val Phe Lys Arg
    1595                1600                1605

Asp Ala Gln Gly Gln Gln Met Ile Phe Pro Tyr Tyr Gly His Glu
    1610                1615                1620

Glu Glu Leu Arg Lys His Pro Ile Lys Arg Ser Thr Val Gly Trp
    1625                1630                1635

Ala Thr Ser Ser Leu Leu Pro Gly Thr Ser Gly Gly Arg Gln Arg
    1640                1645                1650

Arg Glu Leu Asp Pro Met Asp Ile Arg Gly Ser Ile Val Tyr Leu
    1655                1660                1665
```

-continued

```
Glu Ile Asp Asn Arg Gln Cys Val Gln Ser Ser Ser Gln Cys Phe
    1670                1675                1680
Gln Ser Ala Thr Asp Val Ala Ala Phe Leu Gly Ala Leu Ala Ser
    1685                1690                1695
Leu Gly Ser Leu Asn Ile Pro Tyr Lys Ile Glu Ala Val Lys Ser
    1700                1705                1710
Glu Pro Val Glu Pro Pro Leu Pro Ser Gln Leu His Leu Met Tyr
    1715                1720                1725
Val Ala Ala Ala Ala Phe Val Leu Leu Phe Phe Val Gly Cys Gly
    1730                1735                1740
Val Leu Leu Ser Arg Lys Arg Arg Gln His Gly Gln Leu Trp
    1745                1750                1755
Phe Pro Glu Gly Phe Lys Val Ser Glu Ala Ser Lys Lys Lys Arg
    1760                1765                1770
Arg Glu Pro Leu Gly Glu Asp Ser Val Gly Leu Lys Pro Leu Lys
    1775                1780                1785
Asn Ala Ser Asp Gly Ala Leu Met Asp Asp Asn Gln Asn Glu Trp
    1790                1795                1800
Gly Asp Glu Asp Leu Glu Thr Lys Lys Phe Arg Phe Glu Glu Pro
    1805                1810                1815
Val Val Leu Pro Asp Leu Ser Asp Gln Thr Asp His Arg Gln Trp
    1820                1825                1830
Thr Gln Gln His Leu Asp Ala Ala Asp Leu Arg Met Ser Ala Met
    1835                1840                1845
Ala Pro Thr Pro Pro Gln Gly Glu Val Asp Ala Asp Cys Met Asp
    1850                1855                1860
Val Asn Val Arg Gly Pro Asp Gly Phe Thr Pro Leu Met Ile Ala
    1865                1870                1875
Ser Cys Ser Gly Gly Gly Leu Glu Thr Gly Asn Ser Glu Glu Glu
    1880                1885                1890
Glu Asp Ala Pro Ala Val Ile Ser Asp Phe Ile Tyr Gln Gly Ala
    1895                1900                1905
Ser Leu His Asn Gln Thr Asp Arg Thr Gly Glu Thr Ala Leu His
    1910                1915                1920
Leu Ala Ala Arg Tyr Ser Arg Ser Asp Ala Ala Lys Arg Leu Leu
    1925                1930                1935
Glu Ala Ser Ala Asp Ala Asn Ile Gln Asp Asn Met Gly Arg Thr
    1940                1945                1950
Pro Leu His Ala Ala Val Ser Ala Asp Ala Gln Gly Val Phe Gln
    1955                1960                1965
Ile Leu Leu Arg Asn Arg Ala Thr Asp Leu Asp Ala Arg Met His
    1970                1975                1980
Asp Gly Thr Thr Pro Leu Ile Leu Ala Ala Arg Leu Ala Val Glu
    1985                1990                1995
Gly Met Leu Glu Asp Leu Ile Asn Ser His Ala Asp Val Asn Ala
    2000                2005                2010
Val Asp Asp Leu Gly Lys Ser Ala Leu His Trp Ala Ala Ala Val
    2015                2020                2025
Asn Asn Val Asp Ala Ala Val Val Leu Leu Lys Asn Gly Ala Asn
    2030                2035                2040
Lys Asp Met Gln Asn Asn Lys Glu Glu Thr Pro Leu Phe Leu Ala
    2045                2050                2055
```

```
Ala Arg Glu Gly Ser Tyr Glu Thr Ala Lys Val Leu Leu Asp His
    2060                2065            2070

Phe Ala Asn Arg Asp Ile Thr Asp His Met Asp Arg Leu Pro Arg
    2075                2080            2085

Asp Ile Ala Gln Glu Arg Met His His Asp Ile Val Arg Leu Leu
    2090                2095            2100

Asp Glu Tyr Asn Leu Val Arg Ser Pro Gln Leu His Gly Thr Ala
    2105                2110            2115

Leu Gly Gly Thr Pro Thr Leu Ser Pro Thr Leu Cys Ser Pro Asn
    2120                2125            2130

Gly Tyr Leu Gly Asn Leu Lys Ser Ala Thr Gln Gly Lys Lys Ala
    2135                2140            2145

Arg Lys Pro Ser Thr Lys Gly Leu Ala Cys Gly Ser Lys Glu Ala
    2150                2155            2160

Lys Asp Leu Lys Ala Arg Arg Lys Lys Ser Gln Asp Gly Lys Gly
    2165                2170            2175

Cys Leu Leu Asp Ser Ser Ser Met Leu Ser Pro Val Asp Ser Leu
    2180                2185            2190

Glu Ser Pro His Gly Tyr Leu Ser Asp Val Ala Ser Pro Pro Leu
    2195                2200            2205

Leu Pro Ser Pro Phe Gln Gln Ser Pro Ser Met Pro Leu Ser His
    2210                2215            2220

Leu Pro Gly Met Pro Asp Thr His Leu Gly Ile Ser His Leu Asn
    2225                2230            2235

Val Ala Ala Lys Pro Glu Met Ala Ala Leu Ala Gly Gly Ser Arg
    2240                2245            2250

Leu Ala Phe Glu Pro Pro Pro Arg Leu Ser His Leu Pro Val
    2255                2260            2265

Ala Ser Ser Ala Ser Thr Val Leu Ser Thr Asn Gly Thr Gly Ala
    2270                2275            2280

Met Asn Phe Thr Val Gly Ala Pro Ala Ser Leu Asn Gly Gln Cys
    2285                2290            2295

Glu Trp Leu Pro Arg Leu Gln Asn Gly Met Val Pro Ser Gln Tyr
    2300                2305            2310

Asn Pro Leu Arg Pro Gly Val Thr Pro Gly Thr Leu Ser Thr Gln
    2315                2320            2325

Ala Ala Gly Leu Gln His Ser Met Met Gly Pro Leu His Ser Ser
    2330                2335            2340

Leu Ser Thr Asn Thr Leu Ser Pro Ile Ile Tyr Gln Gly Leu Pro
    2345                2350            2355

Asn Thr Arg Leu Ala Thr Gln Pro His Leu Val Gln Thr Gln Gln
    2360                2365            2370

Val Gln Pro Gln Asn Leu Gln Leu Gln Pro Gln Asn Leu Gln Pro
    2375                2380            2385

Pro Ser Gln Pro His Leu Ser Val Ser Ser Ala Ala Asn Gly His
    2390                2395            2400

Leu Gly Arg Ser Phe Leu Ser Gly Glu Pro Ser Gln Ala Asp Val
    2405                2410            2415

Gln Pro Leu Gly Pro Ser Ser Leu Pro Val His Thr Ile Leu Pro
    2420                2425            2430

Gln Glu Ser Gln Ala Leu Pro Thr Ser Leu Pro Ser Ser Met Val
    2435                2440            2445
```

```
Pro Pro Met Thr Thr Thr Gln Phe Leu Thr Pro Pro Ser Gln His
    2450                2455               2460

Ser Tyr Ser Ser Ser Pro Val Asp Asn Thr Pro Ser His Gln Leu
    2465                2470               2475

Gln Val Pro Glu His Pro Phe Leu Thr Pro Ser Pro Glu Ser Pro
    2480                2485               2490

Asp Gln Trp Ser Ser Ser Ser Pro His Ser Asn Ile Ser Asp Trp
    2495                2500               2505

Ser Glu Gly Ile Ser Ser Pro Pro Thr Thr Met Pro Ser Gln Ile
    2510                2515               2520

Thr His Ile Pro Glu Ala Phe Lys
    2525                2530

<210> SEQ ID NO 2
<211> LENGTH: 23
<212> TYPE: PRT
<213> ORGANISM: Artificial Sequence
<220> FEATURE:
<223> OTHER INFORMATION: Synthetic construct

<400> SEQUENCE: 2

Met Pro Arg Leu Leu Thr Pro Leu Leu Cys Leu Thr Leu Leu Pro Ala
1               5                   10                  15

Leu Ala Ala Arg Gly Leu Arg
                20
```